US008880207B2

(12) United States Patent
Abeyratne et al.

(10) Patent No.: US 8,880,207 B2
(45) Date of Patent: Nov. 4, 2014

(54) MULTI-PARAMETRIC ANALYSIS OF SNORE SOUNDS FOR THE COMMUNITY SCREENING OF SLEEP APNEA WITH NON-GAUSSIANITY INDEX

(75) Inventors: Udantha Abeyratne, Forset Lake (AU); Asela Samantha Karunajeewa, Grand Saconnex (CH); Houman Ghaemmaghami, Greenslopes (AU)

(73) Assignee: The University of Queensland, Brisbane, Queensland (AU)

( * ) Notice: Subject to any disclaimer, the term of this patent is extended or adjusted under 35 U.S.C. 154(b) by 551 days.

(21) Appl. No.: 13/139,052

(22) PCT Filed: Dec. 10, 2009

(86) PCT No.: PCT/AU2009/001609
§ 371 (c)(1),
(2), (4) Date: Sep. 14, 2011

(87) PCT Pub. No.: WO2010/066008
PCT Pub. Date: Jun. 17, 2010

(65) Prior Publication Data
US 2012/0004749 A1   Jan. 5, 2012

(30) Foreign Application Priority Data

Dec. 10, 2008  (AU) ................................ 2008906383
Apr. 9, 2009   (AU) ................................ 2009901558

(51) Int. Cl.
*G06F 17/00* (2006.01)
*G10L 25/90* (2013.01)
*A61B 7/00* (2006.01)
*A61B 5/00* (2006.01)

(52) U.S. Cl.
CPC ............... *G10L 25/90* (2013.01); *A61B 5/7267* (2013.01); *A61B 7/003* (2013.01); *A61B 5/4818* (2013.01)

USPC .......................................................... 700/94

(58) Field of Classification Search
None
See application file for complete search history.

(56) References Cited

U.S. PATENT DOCUMENTS 4,776,345 A * 10/1988 Cohen et al. .................. 600/544
4,982,738 A *  1/1991 Griebel ......................... 600/483
(Continued)

OTHER PUBLICATIONS

Abeyratne et al. Proceedinqs of the International Conference on Information and Automation, Dec. 15-18, 2005, Colombo, Sri Lanka, pp. 25-30, "Sleep Apnoea: a Serious Public Health Concern with Tough Information Processing Challenges.".*

(Continued)

*Primary Examiner* — Fan Tsang
*Assistant Examiner* — David Siegel
(74) *Attorney, Agent, or Firm* — Nixon & Vanderhye P.C.

(57) ABSTRACT

An apparatus for diagnosing sleep disorders such as OASHS from snore sounds includes a segmentation module (126) coupled to a data logger (124) to provide segments of the digitized audio signal to a Snore Segment Identifier (128). A total airways response (TAR) module (130), pitch calculator (132), and MFCC calculator (134) are each coupled to an output side of the snore segment identifier module (128). Each of these modules is respectively arranged to calculate pitch, bispectrum, diagonal slice, and MFCC parameters for the snore segments received from the snore segment identifier (128). Similarly, the NGI calculator (136) produces a non-Gaussianity index for the digitized audio signal. A classification module (144) is arranged to process the calculated parameters and compare a resulting diagnosis probability to a predetermined threshold value. The results of this comparison are then indicated on video display (142), which communicates with the classification module (133) via display controller (140) and bus (145). For example, if the results of the comparison are over threshold then display (142) is driven to indicate "OS AHS is present."

23 Claims, 18 Drawing Sheets

(56) References Cited

U.S. PATENT DOCUMENTS

| | | | |
|---|---|---|---|
| 2005/0043645 | A1 | 2/2005 | Ono et al. |
| 2007/0096927 | A1* | 5/2007 | Albert .................... 340/573.1 |
| 2007/0287896 | A1 | 12/2007 | Derchak et al. |
| 2010/0102971 | A1* | 4/2010 | Virtanen et al. .............. 340/575 |

OTHER PUBLICATIONS

Fernandez et al. (GAPS: Siqnal, Systems & RadioComm. Dept., Universidad Politecnica de Madrid, Ciudad Universitaria Madrid Spain and ATVS Biometric Recoqnition Group and Universidad Autonoma de Madrid Spain, pp. 1785-1790, "Design of a multimodal database for research on automatic detection of severe apnoea cases," May 26-Jun. 1, 2008.*

Alshebeili et al. IEEE Transactions on Circuits and Systems—11: Analog and Digital Signal Processing, vol. 39, No. 9, Sep. 1992, pp. 634-637 "Identification of Nonminimum Phase MA Systems Using Cepstral Operations on Slices of Higher Order Spectra".*

Sola-Soler et al. Proceedings of the 29th Annual International Conference of the IEEE EMBS Cité Internationale, Lyon, France Aug. 23-26, 2007, pp. 6093-6096, "Automatic classification of subjects with and without Sleep Apnea through snoring analysis".*

Al-Ani, Tarik, et al, *Proceedings of the 2005 IEEE Conference on Control Applications*, Toronto, Canada, Aug. 28-31, 2005, pp. 1099-1103, "A Stochastic Learning Based Approach for Automatic Medical Diagnosis Using HMM Toolbox in Scilab Environment."

Abeyratne, Udantha R., et al, *Proceedings of the International Conference on Information and Automation*, Dec. 15-18, 2005, Colombo, Sri Lanka, pp. 25-30, "Sleep Apnoea: a Serious Public Health Concern with Tough Information Processing Challenges."

Abeyratne, U.R., et al, *School of Electrical and Electronic Engineering*, Nanyang Technological University, Singapore, 5 pages, "Pitch-Jitter Analysis of Snoring Sounds for the Diagnosis of Sleep Apnea," Oct. 25, 2001.

Fernandez, Ruben, et al, *GAPS: Signal, Systems & RadioComm. Dept., Universidad Politecnica de Madrid, Ciudad Universitaria, Madrid, Spain; and Respiratory Dept. Unidad de Trastornos Respiratorios del Sueno, Hospital Clinico Universitario Malaga, Spain, and ATVS Biometric Recognition Group, Universidad Autonoma de Madrid, Spain*, pp. 1785-1790, "Design of a multimodal database for research on automatic detection of severe apnoea cases," May 26-Jun. 1, 2008 (Conference LREC '08).

International Application for PCT/AU2009/001609, mailed Feb. 8, 2010.

Written Opinion for PCT/AU2009/001609, mailed Feb. 8, 2010.

\* cited by examiner

MULTI-PARAMETRIC ANALYSIS OF SNORE SOUNDS FOR THE COMMUNITY SCREENING OF SLEEP APNEA WITH NON-GAUSSIANITY INDEX

This application is the U.S. national phase of International Application No. PCT/AU2009/001609 filed 10 Dec. 2009 which designated the U.S. and claims priority to AU Patent Application Nos. 2008906383 filed 10 Dec. 2008 and 2009901558 filed 9 Apr. 2009, the entire contents of each of which are hereby incorporated by reference.

I. FIELD OF THE INVENTION

The present invention relates to a method for diagnosing sleep disorders. More specifically, a preferred embodiment of the present invention is suitable for diagnosing obstructive sleep apnea in a subject with reference to sounds made by the subject.

II. BACKGROUND

Obstructive Sleep Apnea Hypopnea Syndrome (OSAHS) is a highly prevalent disease where snoring is one of the most common symptoms. OSAHS occurs during sleep due to collapsing of upper airways leading to cessation of breathing. The narrowing of airways and the relaxed muscles surrounding the airways generally results in snoring. OSAHS is a classic example for a treatable disease, which, by it self is not life-threatening. However, if left untreated, it causes an avalanche of devastating complications such as reduction in cognitive function, cardiovascular diseases, decreased quality of life, fatigue and increased vulnerability to accidents [1].

Full closure of the airways is known as obstructive sleep apnea and a partial closure is defined as obstructive hypopnea. OSAHS severity is expressed by the Apnea-Hypopnea-Index (AHI), which computes the number of Apnea and Hypopnea events per hour, averaged over the total sleep time. The following conventions are currently in clinical use: AHI<5 (no OSAHS), 5<AHI<15 (mild OSAHS), 15<AHI<30 (moderate OSAHS) and AHI>30 (severe OSAHS). Some researchers also use AHI=10 as the threshold for diagnosing the disease.

The current accepted diagnosis for OSAHS is by supervised overnight Polysomnography (PSG) to record a multitude of physiological signals for manual analysis at a sleep laboratory. Thus it is very expensive and time consuming. Limited PSG facilities around the world have resulted in long waiting lists and over 80%-90% individuals with OSAHS currently remain undiagnosed in Australia [2].

There has been a flurry of recent activities at developing technology to address this need [3 and references therein] for simplified diagnostic methods. The main focus of these activities was the development of ambulatory sleep instrumentation hardware.

The National Sleep Disorders Research Plan [4], USA, 2003, reports that the single-signal and full PSG systems meant for home monitoring yielded mixed results, and that none was sufficiently effective for routine use. One of the main problems faced by such devices is that the service of an experienced medical technologist is still required at the site of the test, if acceptable sensitivity/specificity performance is required.

It is an object of the invention to provide a method and apparatus for diagnosing a sleeping disorder in a subject that is an improvement, or at least a useful alternative, to the previously surveyed approaches of the prior art.

III. SUMMARY OF THE INVENTION

According to a first aspect of the present invention there is provided a method for diagnosing a sleeping disorder in a subject, for example OSAHS, including:
processing a digitized audio signal from the subject with at least one electronic processor, said processing including:
estimating values for one or more parameters of said audio signal;
applying the values to a predetermined diagnostic model; and
indicating the presence of a sleeping disorder based on the output of said model;
wherein the plurality of parameters include one or more of: pitch parameters, higher order spectrum parameters, cepstral coefficients, slice parameters, a Gaussianity distribution parameter.

In a preferred embodiment the cepstral coefficients are mel-frequency cepstral coefficients, the slice parameters are diagonal slice parameters, the higher order spectrum parameters are bispectrum parameters, the Guassianity distribution parameter is a non-Gaussianity index.

Preferably the step of processing the digitized audio signal includes a step of segmenting said audio signal into a plurality of segments.

The predetermined diagnostic model comprises a logistic regression model although other pattern classifiers may be used as alternatives.

In one embodiment the one or more parameters include
two pitch parameters;
two bispectral parameters;
four mel-frequency cepstral coefficients; and
three diagonal slice parameters.

Preferably the step of processing the digitized audio signal from the subject includes dividing the digitized signal into a plurality of segments.

The method may include a step of identifying said segments indicating voiced snoring prior to the step of estimating values for the plurality of parameters.

Preferably the presence of the sleeping disorder is indicated on an electronic display coupled to a computer incorporating the at least one electronic processor.

The one or more parameters may include the non-Gaussian distribution parameter and the method may include:
dividing the digitized audio signal into a number of segments;
calculating indices indicating a degree of Gaussianity corresponding to each of the segments; and
computing a parameter indicating overall Gaussianity of the said signal based on the indices.

Preferably the step of calculating indices indicating a degree of Gaussianity includes calculating a normal probability of each said segment of the digitized audio signal.

In a preferred embodiment the method includes a step of pre-emphasis filtering of the digitized audio signal to relatively boost energy of portions of the digitized audio signal corresponding to snoring episodes of the subject.

The step of pre-emphasis filtering of the digitized audio signal may include applying a digital high pass filter to said signal.

Preferably the method includes a step of comparing the indices indicating a degree of Gaussianity to a predetermined threshold value.

The method may include receiving a user input to select the predetermined threshold value from a range of predetermined threshold values calculated to optimize for desired negative predictive values and positive predictive values.

Preferably the method includes a step of discarding end portions of the digitized audio signal contaminated with non-sleep related noise.

According to a further aspect of the present invention there is provided an apparatus for diagnosing a sleeping disorder in a subject including:

at least one digital signal input point for receiving a digitized audio signal of the subject;

at least one electronic processor in communication with the digital signal input point;

a user display viewable by an operator of the apparatus; and at least one electronic memory in communication with the electronic processor, said electronic memory containing tangible instructions executable by the said electronic processor, said instructions being;

to detect snore segments of the digitized audio signal;

to estimate values for a plurality of parameters of the snore segments, said parameters including one or more of: pitch parameters, higher order spectrum parameters, cepstral coefficients, slice parameters, a Gaussianity distribution parameter;

to apply the values to a predetermined diagnostic model; and to indicate the presence of a sleeping disorder based on the model upon the user display.

According to a further aspect of the present invention there is provided an apparatus for diagnosing a sleeping disorder in a subject including:

at least one audio signal input point for receiving an audio signal of a sleeping subject;

an analog to digital converter coupled to the audio signal input point to create a digitized audio signal;

a plurality of sleep-related parameter calculation modules responsive to the digitized audio signal and arranged to produce signals indicating values for said sleep-related parameters;

a classification module responsive to the signals indicating values for said sleep-related parameters and arranged to classify the audio signal as either sleep dysfunctional or non-sleep dysfunctional;

a display assembly responsive to the classification module and arranged to display said classification.

Preferably the apparatus includes a data logger to record the digitized audio signal and to record the signals indicating values for said sleep-related parameters.

In a preferred embodiment the assembly includes a segmentation module arranged to segment the digitized audio signal, said segmentation module being disposed in a signal path between the analog to digital converter and the plurality of sleep-related parameter calculation modules.

The sleep-related parameter calculation modules will preferably include one or more of:
a total airways response calculator;
a pitch calculator;
a cepstral coefficient calculator;
a non-Gaussianity Index calculator.

The sleep related parameter calculation modules preferably include the non-Gaussianity Index (NGI) calculator. Preferably the apparatus further includes a pre-emphasis module coupled to an input side of the NGI calculator for filtering the digitized audio signal prior to processing by the NGI calculator.

In a preferred embodiment a user control interface is provided that is coupled to modules of the apparatus to facilitate operator adjustment of said modules.

According to a further aspect of the present invention there is provided a computer software product comprising a program storage device, readable by machine, tangibly embodying a program of instructions executable by the machine to cause the machine to perform the previously mentioned method.

According to another aspect of the present invention there is provided a method for diagnosing a sleeping disorder in a subject including:

recording sleep sounds of the subject with a microphone;

digitizing the sleep sounds with an analog to digital converter to create a digitized audio signal;

calculating a statistical probability distribution index in respect of the digitized audio signal;

applying said index to a predetermined diagnostic model; and indicating the presence of the sleeping disorder to a human operator with an electronic display, based on an output of the model.

According to a further aspect of the invention there is provided a software product comprising a program storage device, readable by machine, tangibly embodying a program of instructions executable by the machine to cause the machine to perform the method.

According to another aspect of the invention there is provided a method for producing a diagnostic model to identify a sleep disorder including:

compiling data from a training set of subjects including subjects known to suffer from the sleep disorder and subjects known to not suffer from the disorder;

processing the data with an electronic processor to generate values for a plurality of parameters corresponding to the data and characterising the Pitch and Total Airways Response of the subjects;

calculating classification model parameters from said values;

displaying the classification model parameters for use by a human operator.

The diagnostic model is preferably a logistic regression model and the step of calculating classification model parameters from said values includes applying logistic regression analysis to the values.

Preferred features, embodiments and variations of the invention may be discerned from the following detailed description of sections V. onwards, which provides sufficient information for those skilled in the art to perform the invention. The detailed description is not to be regarded as limiting the scope of the preceding Summary of the Invention in any way. The detailed description will make reference to a number of Figures throughout as follows.

IV. DESCRIPTION OF THE DRAWINGS

(b) the Sum of magnitudes $B(f_n)$ and (c) Diagonal slice $D_k(f_n)$.

Figure 3:
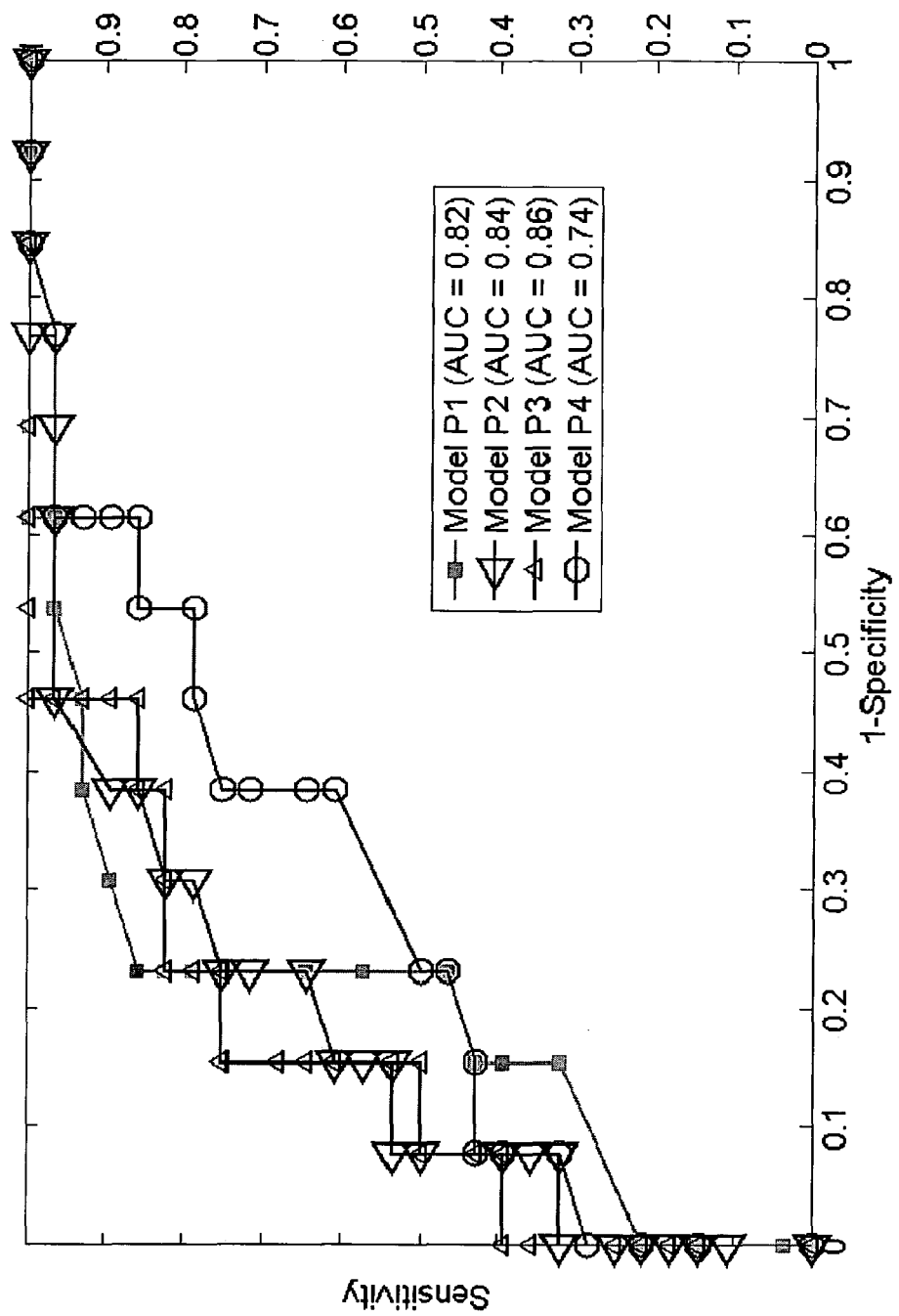

FIG. 3 Depicts the Receiver Operating Characteristic (ROC) curves for individual parameter group models.

Figure 4:
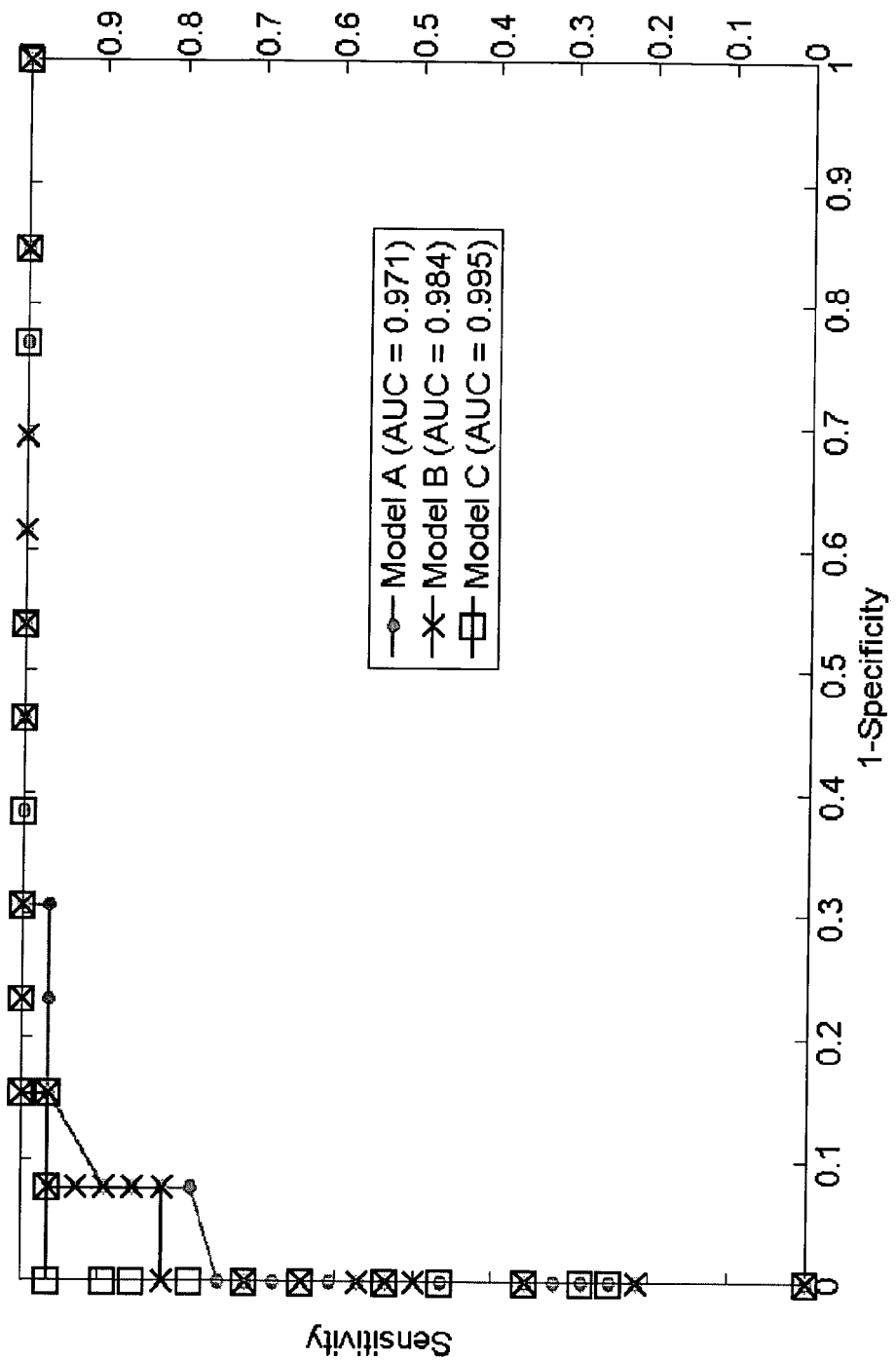

FIG. 4 Depicts Receiver Operating Curves (ROC) for multi-parametric models

Figure 5:
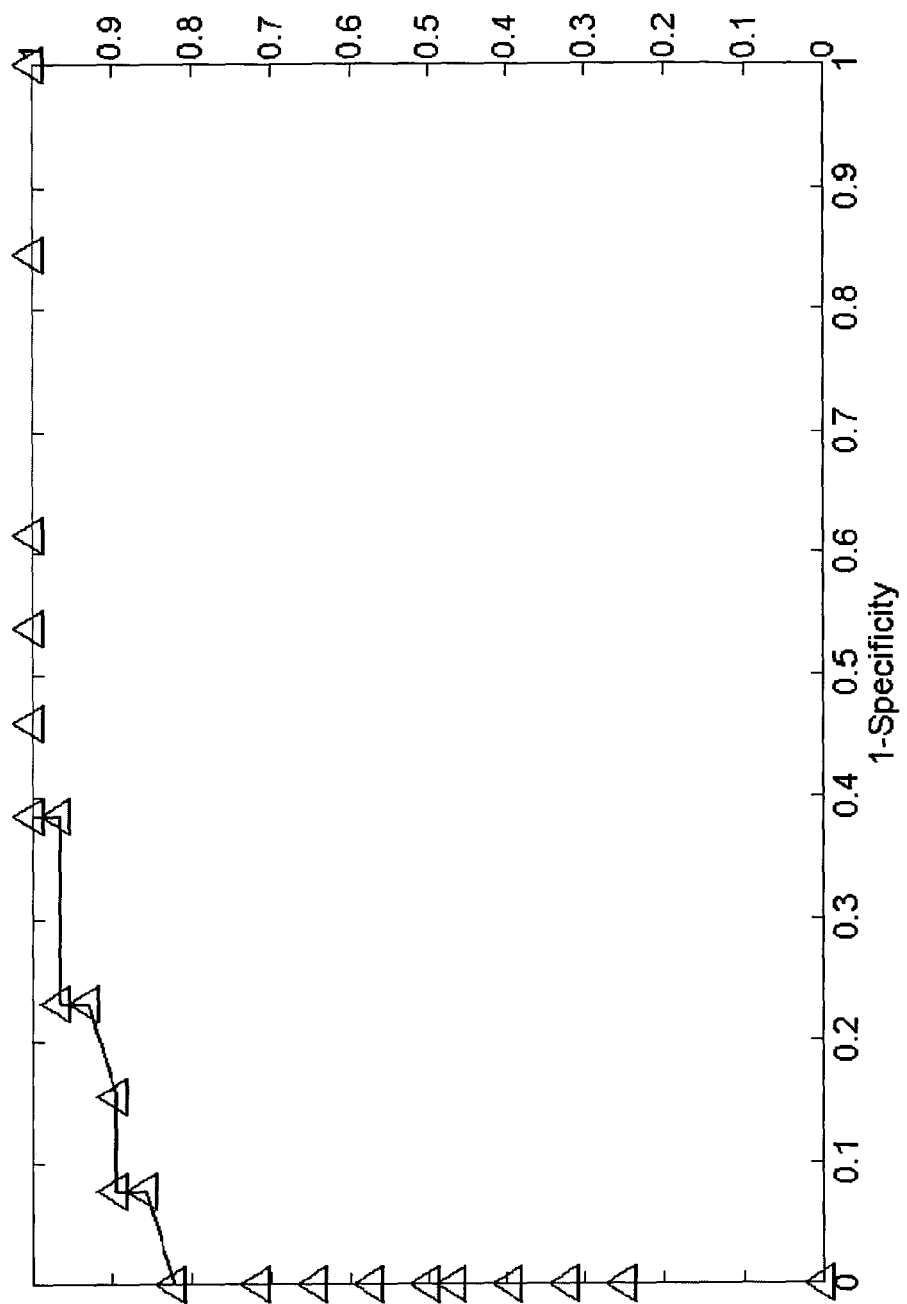

FIG. 5 Depicts Receiver Operating Curves (ROC) for Leave-One-Out Validation of model C.

Figure 6:
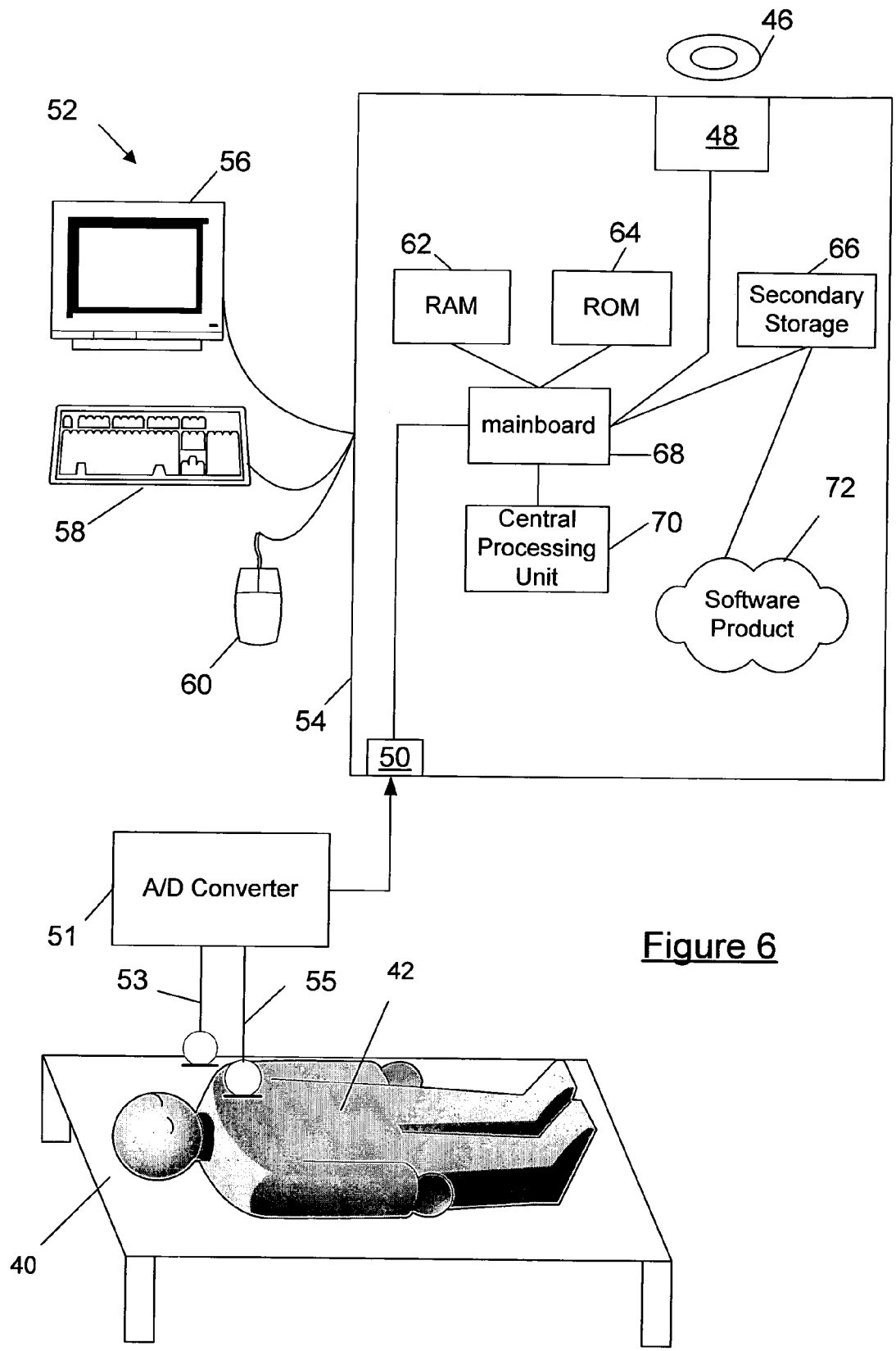

FIG. 6 is a block diagram of a subject being monitored by an apparatus in accordance with an embodiment of the present invention.

Figure 7:
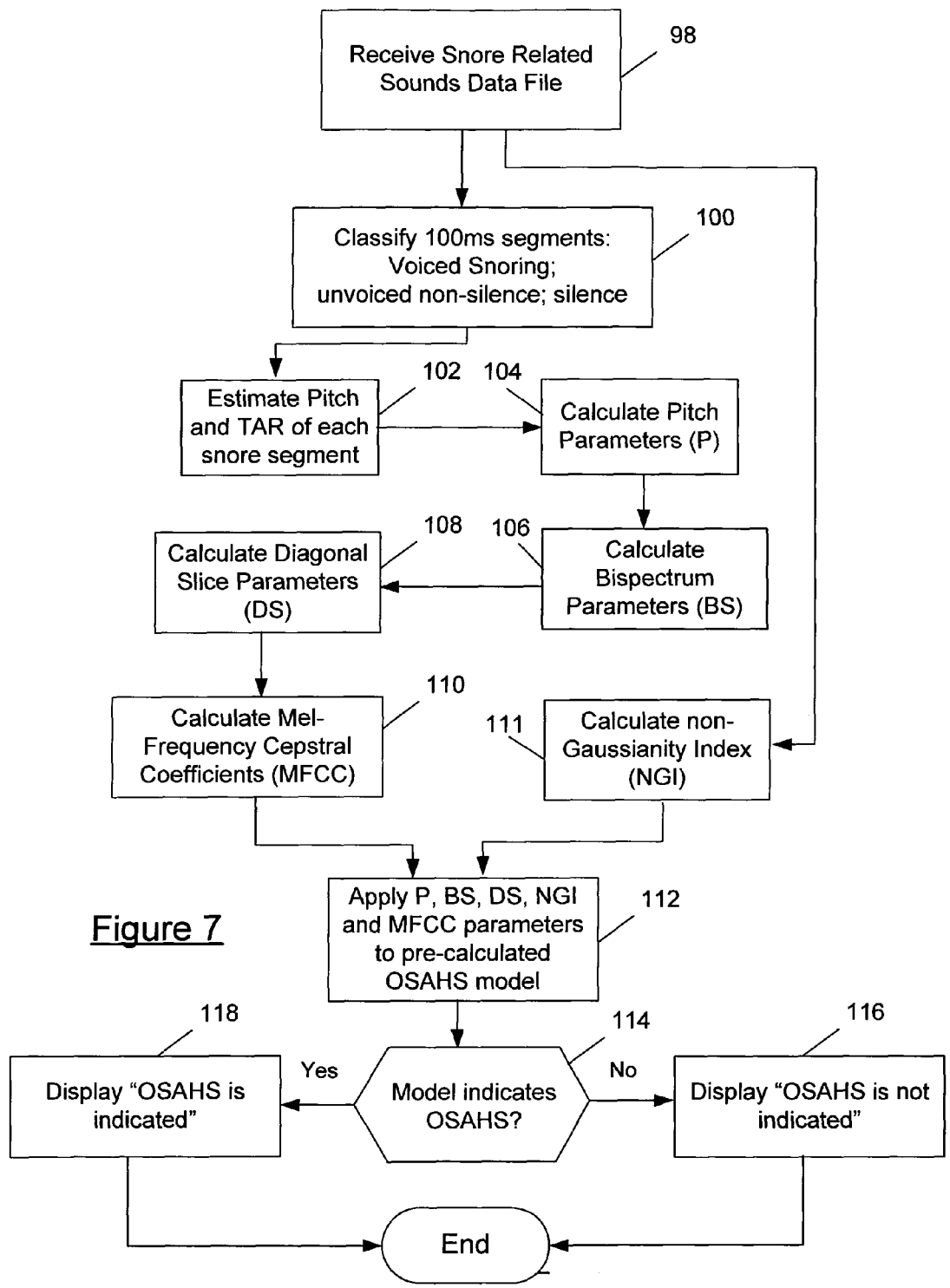

FIG. 7 is a flowchart of a method for diagnosing OSAHS in a subject according to an embodiment of the present invention.

Figure 7A:
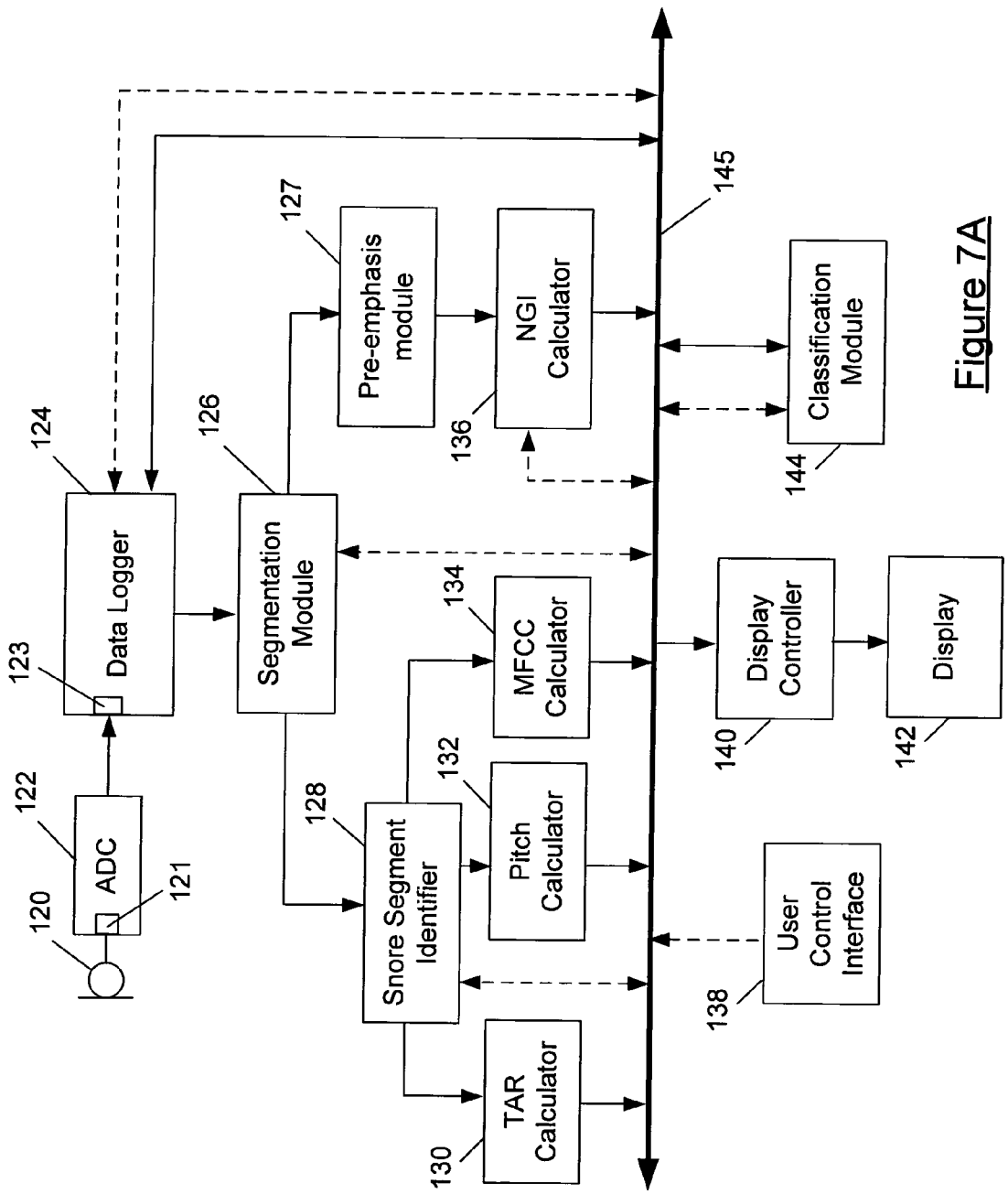

FIG. 7A is a block diagram of an apparatus for diagnosing OSAHS according to an embodiment of the present invention.

Figure 8:
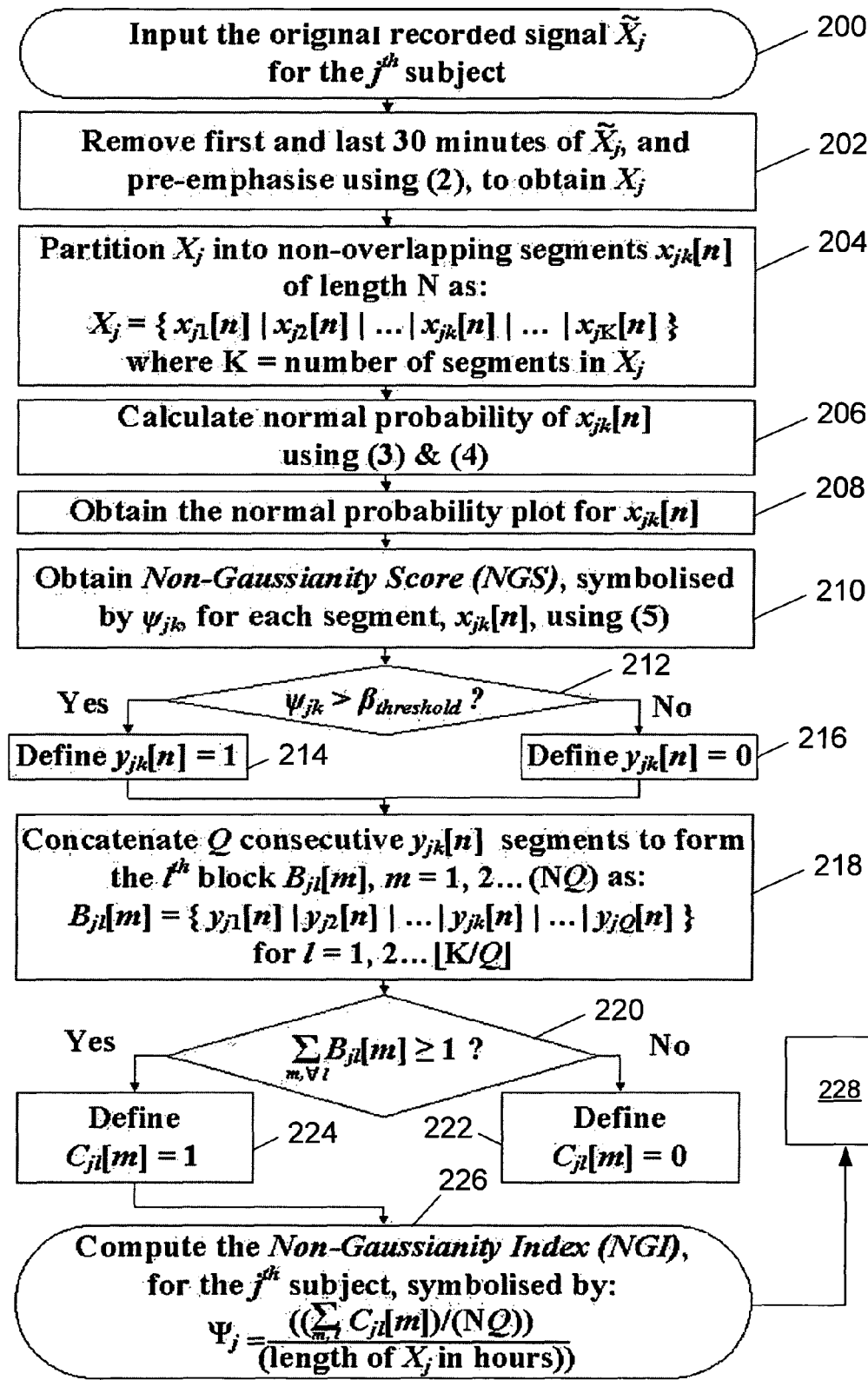

FIG. 8 is a flowchart of a method for determining a non-Gaussianity index for diagnosing OSAHS according to an embodiment of the present invention.

Figure 9:
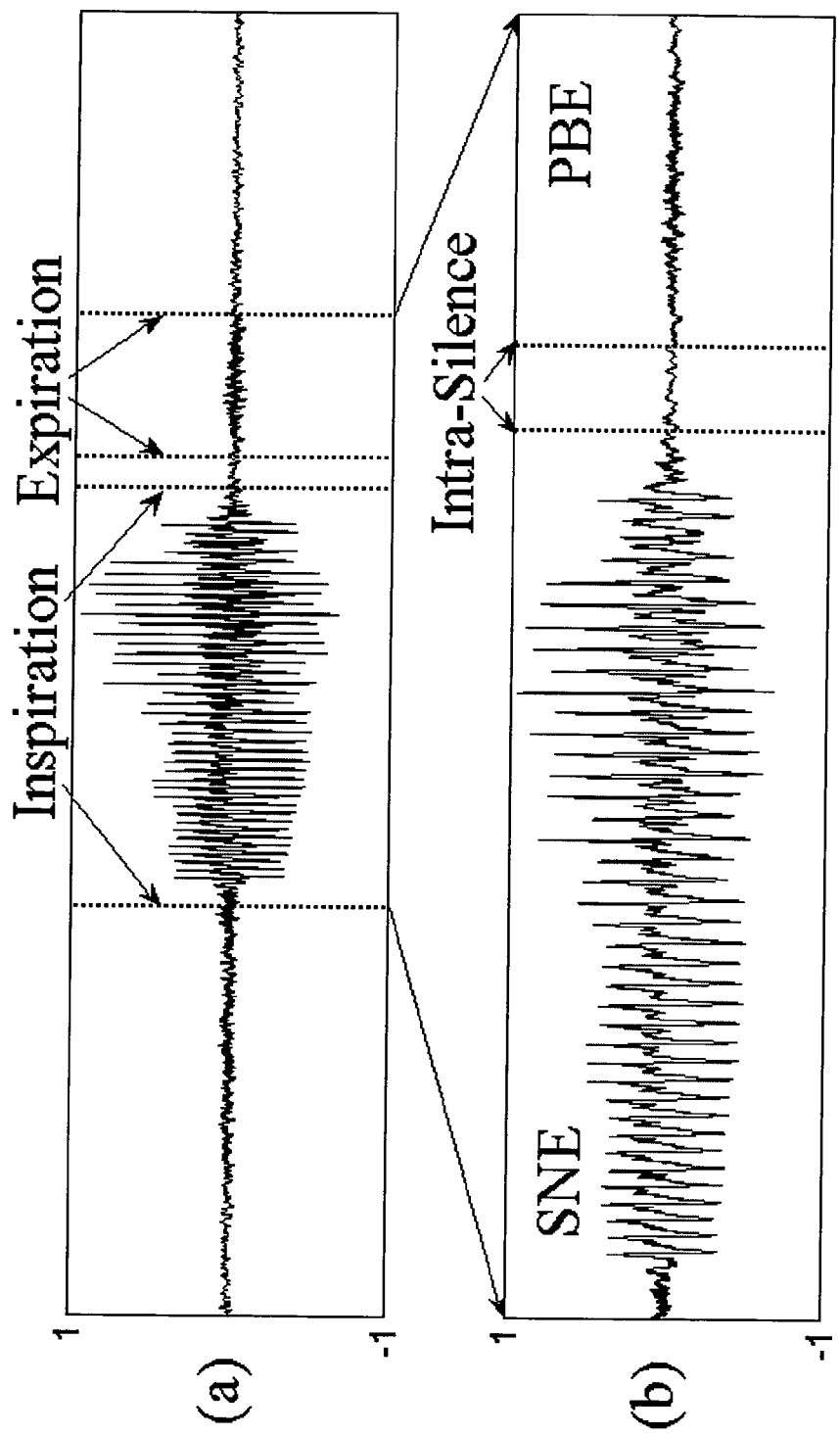

FIG. 9: (a) Displays the input signal x[n] of a recording of a sleeping subject, with the inspiration and expiration sections of the signal marked. (b) Displays the segment of the signal corresponding to the start of the inspiration to the end of the expiration with the breakdown of the signal into the three categories of SNE, Intra-Silence, and PBE.

Figure 10:
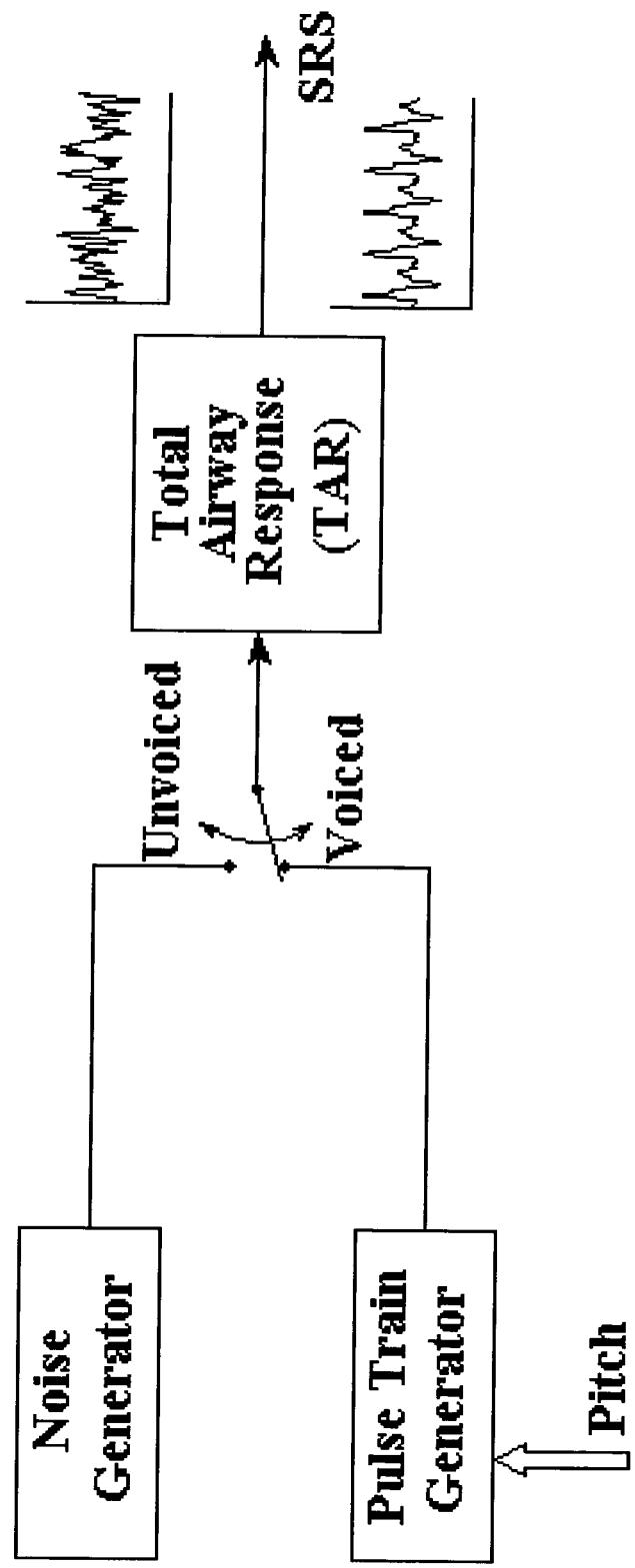

FIG. 10 depicts a model for the production of snore related sounds. Voiced segments are generated using a pulse-train source waveform, while unvoiced segments use a white-noise source.

Figure 11:
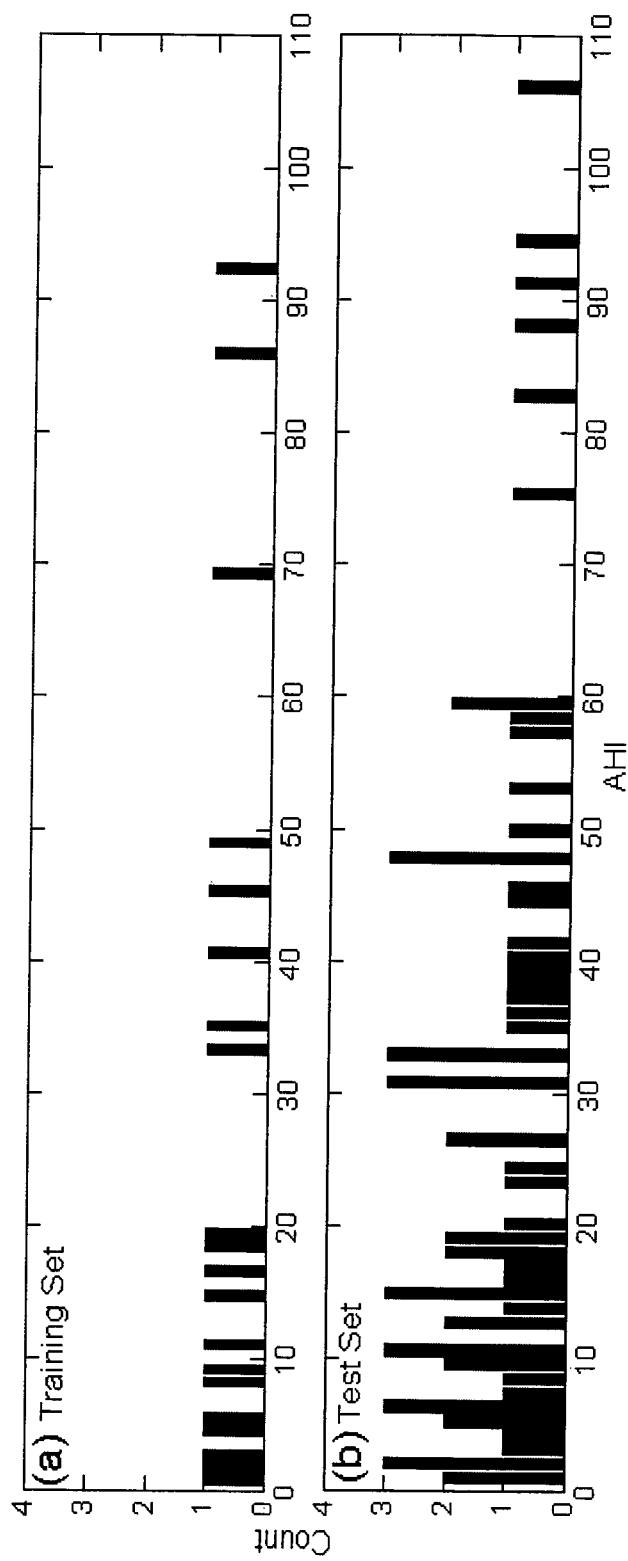

FIG. 11 depicts the AHI distribution of: (a) the training set (20 subjects), and, (b) the testing set (66 subjects) used in testing the performance of the NGI method.

Figure 12:
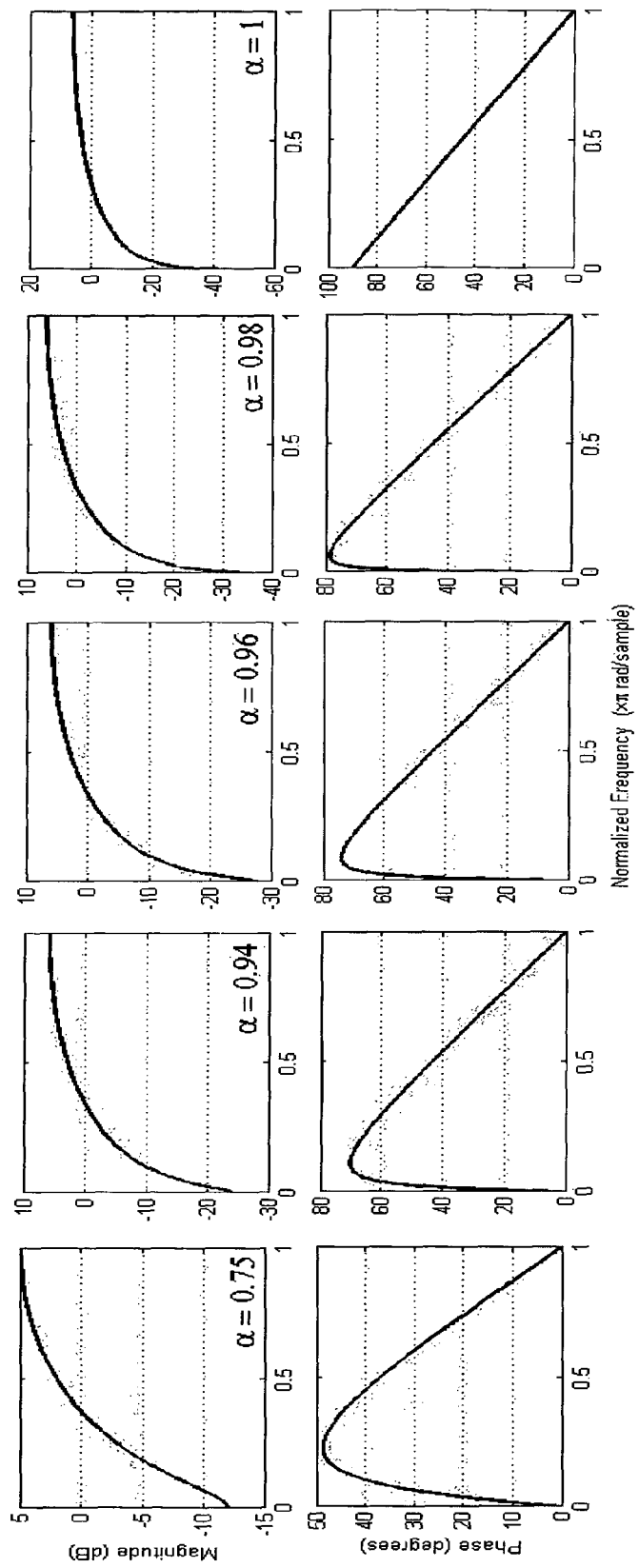

FIG. 12 depicts the frequency response of the pre-emphasis filter used according to a preferred embodiment of the present invention. The figure displays five values of $\alpha$ for which the pre-emphasis filter response is plotted. It can be seen that in the 0.94 to 0.98 region of the graphs little difference is observed. 0.96 provides a mid-point region in the commonly utilised values.

Figure 13:
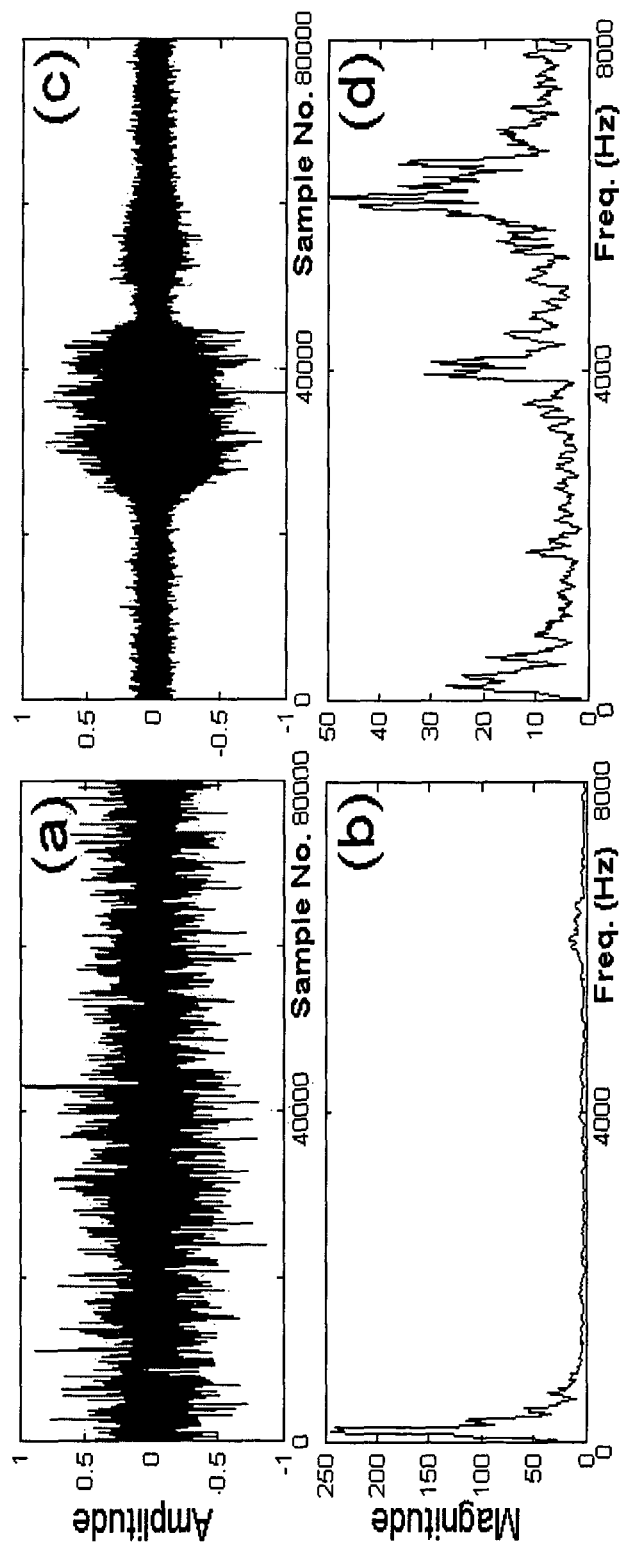

FIG. 13 shows (a) Original voiced and unvoiced snore segment, (b) The frequency domain representation of the data segment in (a), (c) The pre-emphasised time-domain version of the data segment in (a), (d) The frequency domain representation of the time-domain data segment in (c). It can be seen that the pre-emphasis filter corrects the roll-off inspected in the spectrum of the snore segment.

Figure 14:
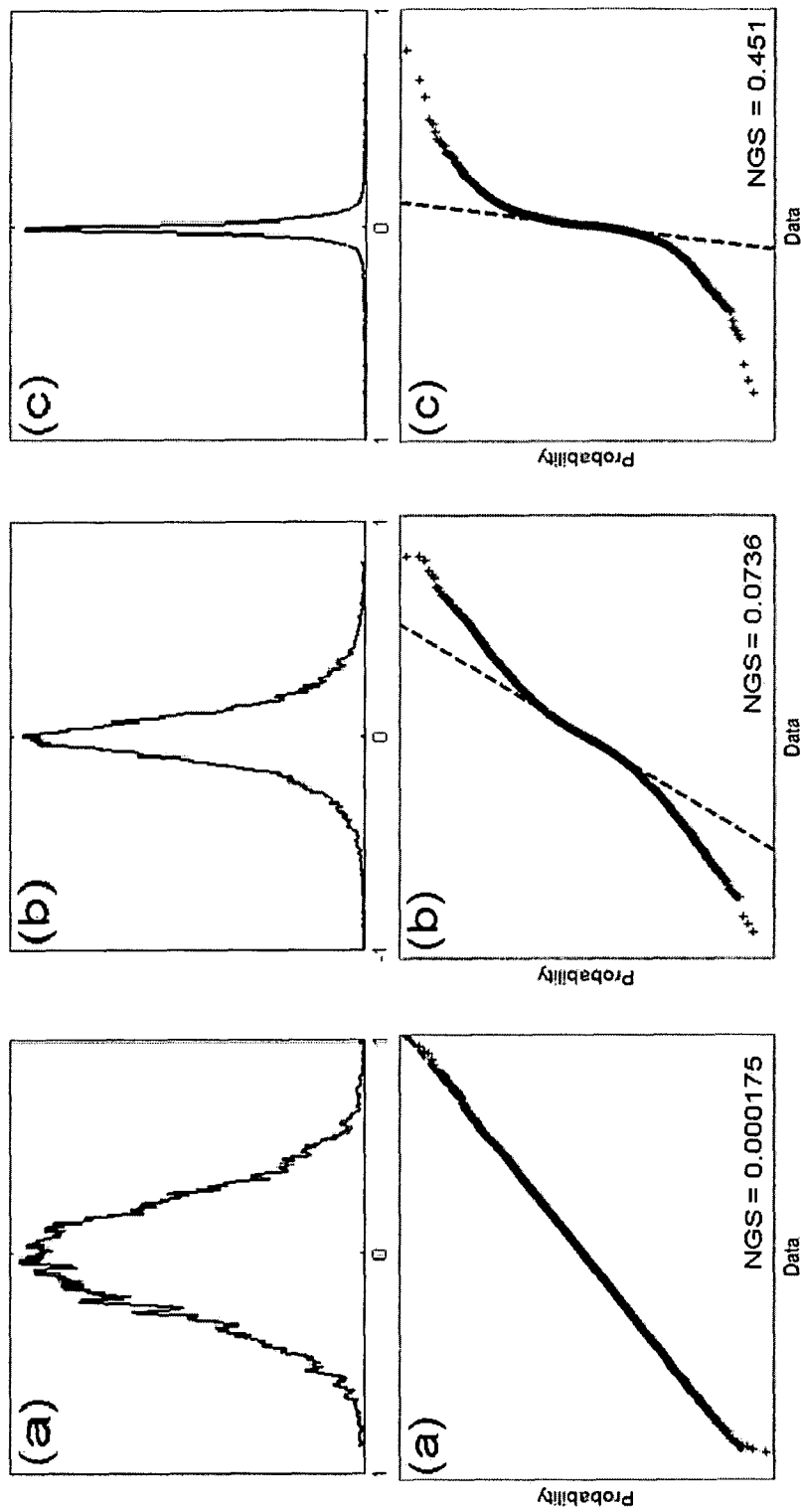

FIG. 14 The energy-normalised distribution templates for a segment of data taken from: (a) a breathing/silence episode, (b) a snoring episode from a non-OSAHS subject, and (c) a snoring episode from an OSAHS subject.

Figure 15:
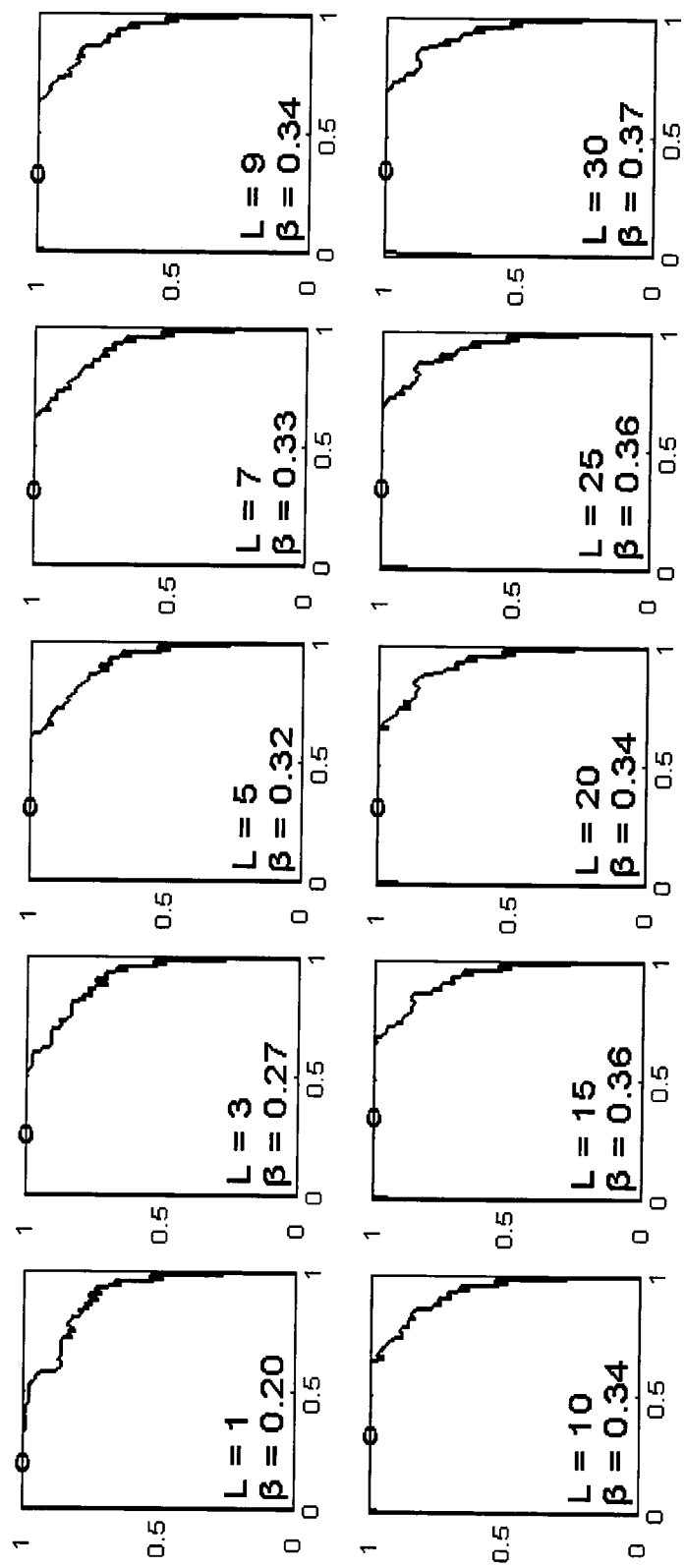

FIG. 15. Area under ROC curve verses $\beta$ graphs. A range of $\beta$ values were utilised ranging from 0 to 1, with a step size of 0.01. Each point on the y-axes of the graphs displays the area under the ROC curve at the $\beta$ threshold indicated by the x-axes. The marked points on each graph display the $\beta$-point that gives maximum detectability using the set L-length partitioning. (The $\beta$ of the marked points is displayed on each graph)

Figure 16:
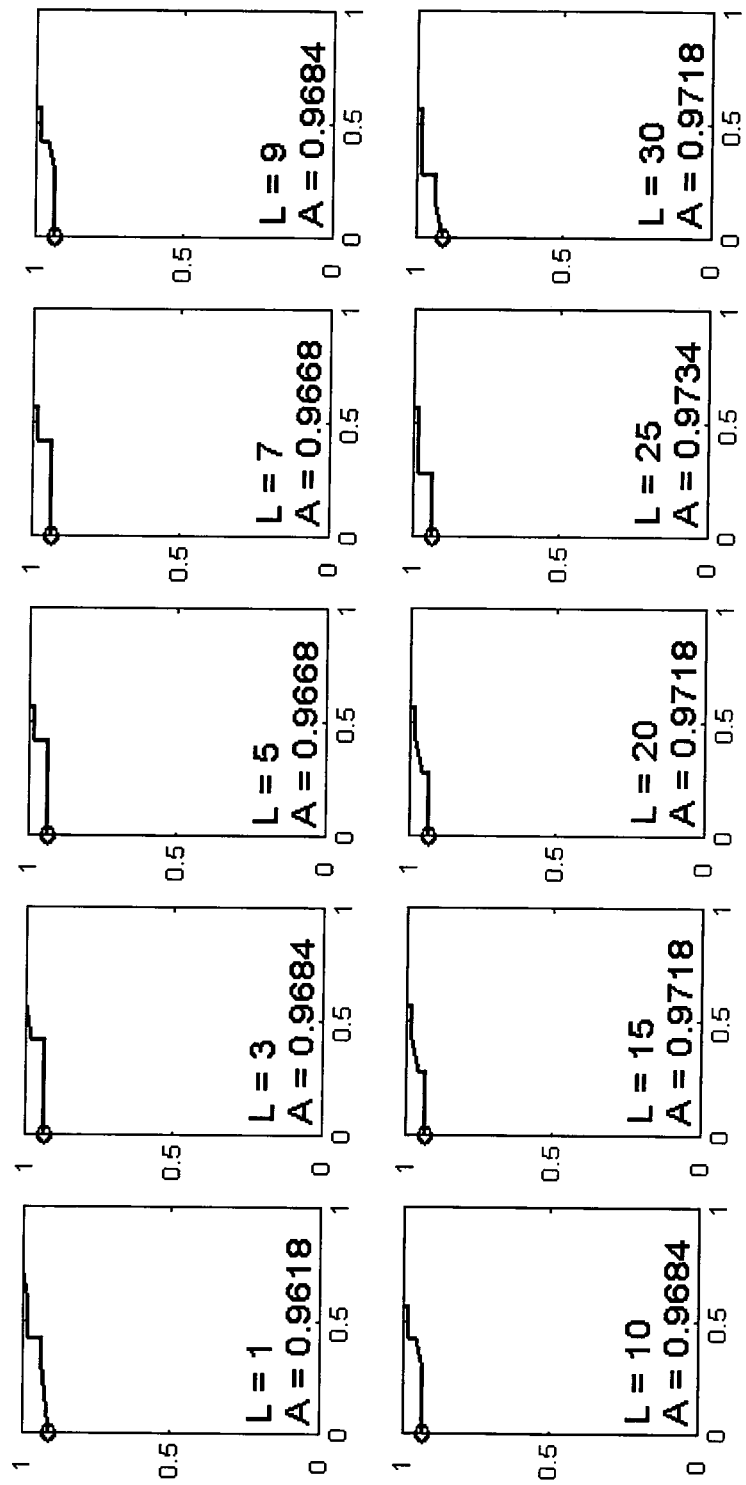

FIG. 16. ROC curves for the 10 L-length partitioning experiments. Each graph represents sensitivity versus (1-specificity). The L value and the area under each curve (A) is marked on the plot.

The A value represents the area under the ROC curve which is known as detectability and was used as one measure of performance in this study. (The point giving optimum positive predictive value (ppv) is marked on each graph).

Figure 17:
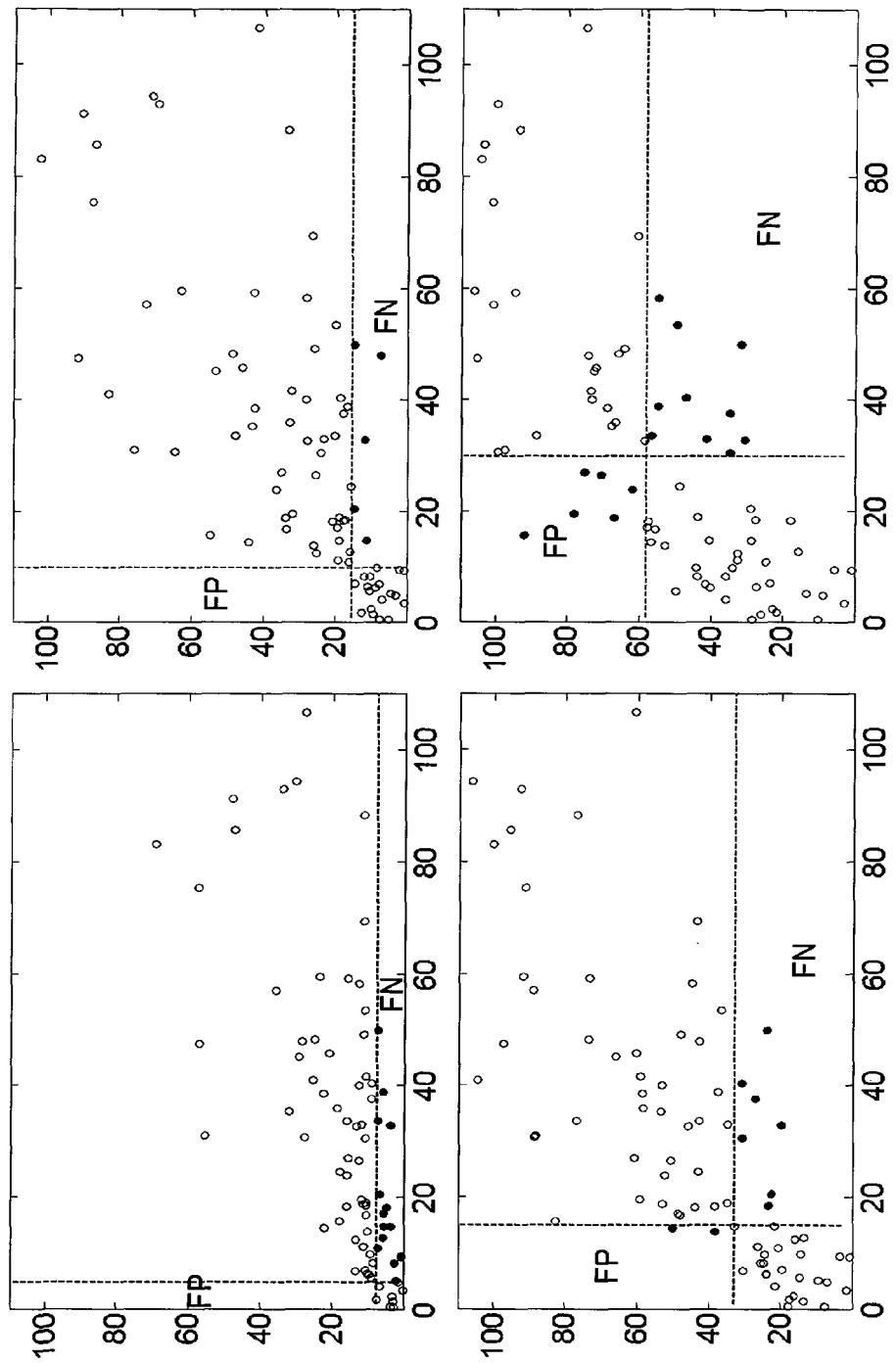

FIG. 17. (a) A graph displaying NGI versus AHI for the 86 test and train subjects, for optimum L and $\beta$ values of 25 s and 0.54, respectively. The NGI threshold for OSA, non-OSAHS discrimination was found to be ($\psi_{thresh}$=7.61). The vertical dashed line marks the (AHI=5) boundary and the horizontal dashed line marks the ($\psi_{thresh}$=7.61) diagnostic edge. The false negative (FN) and false positive (FP) error regions are have been marked on each displayed plot. (b) The graph displaying NGI versus AHI for the 86 test and train subjects, for (AHI=10) used as the diagnostic edge. (c) The graph for (AHI=15). (d) The graph for (AHI=30).

V. DETAILED DESCRIPTION OF PREFERRED EMBODIMENTS

The basic premise of the inventors' work is that snore signals carry vital information which enables the state of the upper airways to be characterized. The inventors have realized that the upper airway acts as an acoustic filter during the production of snoring sounds, just as the vocal tract does in the case of speech sounds. Episodes of sleep disorders and sleep dysfunctions such as OSAHS are, by definition, associated with partial or full collapse of upper airways. As such, the inventors have realized that changes to the upper airways brought about by this collapse should be embedded in snore signals.

VI. SNORE RELATED SOUND DATA ACQUISITION

Snore related sounds (SRS) were initially acquired for later use in training and testing a method according to an embodiment of the invention. Initially snore related sounds (SRS) were acquired simultaneously, but independently, during a routine PSG session at the Respiratory and Sleep Disorders Unit of the Princess Alexandra Hospital, Brisbane, Australia. A pair of low noise microphones having a hypercardiod beam pattern (Model NT3, RODE®, Sydney, Australia) were placed at a nominal distance of 50 cm from the mouth of the patient. A professional quality pre-amplifier and A/D converter unit (Model Mobile-Pre USB, M-Audio®, California, USA) was used for sound signal acquisition, at a sampling rate of 44.1 k samples/s and a bit resolution of 16 bits/sample. The system had a 3 dB bandwidth of 20800 Hz at the sampling rate used. Although it is generally accepted that the bandwidth of snore sounds is about 10 kHz, the sampling rate was kept at 44.1 k samples/s in order to obtain the best sound quality, and to capture, without distortion, any speech segments embedded in SRS sounds.

All night SRS data from 41 subjects (13 normal, 28 OSAHS) was initially studied. Data from each subject was classified into 100 ms segments of voiced non-silence, unvoiced non-silence and silence using an automatic SRS data segmentation method [12]. Following definitions D1-D3 in section VII A., these 100 ms segments were then grouped into episodes. The resulting 39,434 episodes were manually screened for bed noise, Catathrenia (nocturnal groaning) and speech.

From each subject up to a maximum of 100 snore episodes were randomly selected. Pitch and TAR of each 100 ms voiced snore segment within these snore episodes were then estimated using the HOS based method. In some subjects less than 100 episodes of snoring were observed (see Table 1, column 7, where NOE stands for the Number of Episodes analysed). Table 1 shows the summary of subject characteristics and snore episodes used in model derivation.

TABLE 1

Summary of subject characteristics and snore episodes analyzed for model development

| Subjects | N (M/F) | | Age | BMI | AMI | NOE |
|---|---|---|---|---|---|---|
| Simple | 13 | M | 45 | 33.5 | 5.9 | 88 |
| Snorers | (5/8) | SD | 11 | 11 | 2.0 | 17 |
| AHI < 10 | | R | 29-63 | 20.6-49.2 | 1.5-9.8 | 56-100 |
| OSAHS | 28 | M | 54 | 34.5 | 48.66 | 95 |
| AHI > 10 | (23/5) | SD | 14 | 6.1 | 27.08 | 16 |
| | | R | 16-78 | 23.8-48.7 | 13.8-106.7 | 45-100 |

N: Number of subjects (Male/Female) M: Mean SD: Standard deviation R: Range BMI: Body Mass Index AHI: Apnea Hypopnea Index NOE: No of snore episodes analyzed.

VII. METHOD

A. Snore Definition

Previously [11] formalised objective definition of snoring sounds are referred to in this document as defined via (D1)-(D3) below:

(D1) 'Breathing Episode' (BE) is defined as the SRS data from the start of an inspiration to the corresponding end of expiration. This period may also contain small segments of silence, for example, between the end of inspiration and the start of expiration (e.g. time interval 1.7-1.9 in FIG. 1 (*b*)).

(D2) 'Snoring Episode' (SE) is defined as a Breathing Episode with at least one portion of it containing sound with a detectable pitch. The part with detectable pitch is termed a 'voiced snoring segment'. The rest of the Snoring Episode containing sound without pitch is classified as 'unvoiced snoring segment'. Just like in a Breathing Episode, there can be 'silent segments' inside the Snoring Episode. A snoring Episode must consist of at least one voiced-snoring segment (by definition).

(D3) A Breathing Episode that is not a Snoring Episode is called a Pure-Breathing Episode (PBE).

Figure 1:
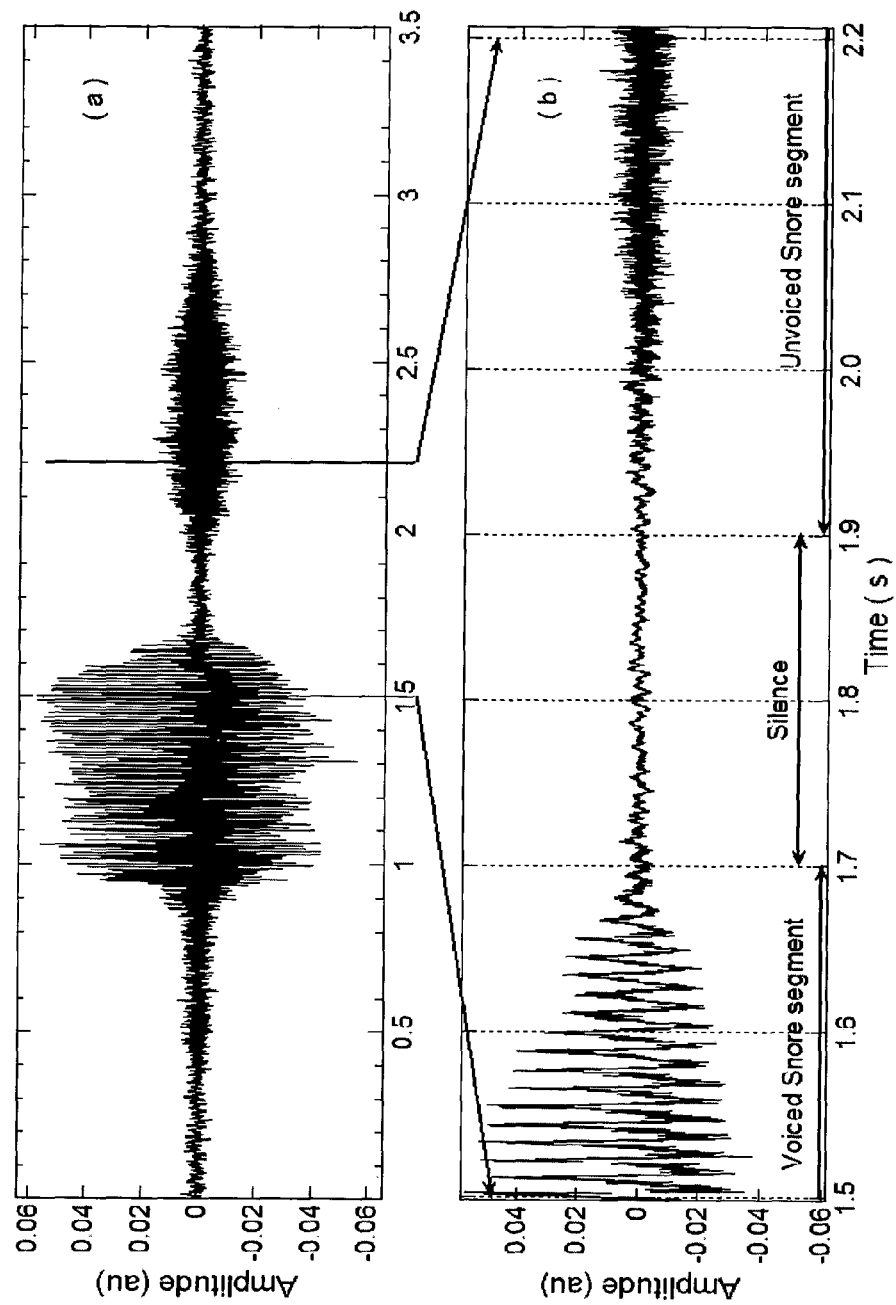
FIG. 1 shows examples of a BE, which is an SE comprising of a 'voiced snoring segment', a 'silent segment' and an 'unvoiced snoring segment.'

FIG. 1 shows examples of a BE, which is an SE comprising of a 'voiced snoring segment', a 'silent segment' and an 'unvoiced snoring segment.'

B. Snore Source/Upper Airway Model

Snoring segments s(n) were modelled as;

$$s(n) = h(n) \bigcirc x(n), \quad (1)$$

the convolution between: (i) 'source signal x(n)' representing the source acoustical energy and, (ii) '(TAR) Total Airway Response h(n)' which captures the acoustical features of the upper airways. In the case of voiced-snore, the source excitation x(n) is best modeled as a pseudo periodic sequence having its origins in the vibrations of the upper-airway structures. Higher Order Statistics (HOS) based methods have been previously described in [11] to jointly estimate the pitch of the source (pseudo periodic sequence) and the TAR of voiced snore segments. Appendix A briefly describes the theoretical derivation of the higher-order spectrum (HOS) based algorithm for joint estimation of pitch and TAR. Pitch and the TAR are used to generate snore parameters (independent variables) for models that are used in various embodiments of the present invention.

C. Parameter Generation from Pitch and TAR

Each snore episode (SE), by definition D2, has at least one segment within it with a definable pitch (periodicity). Within a SE, pitch, the fundamental frequency of vibration changes with time.

In the following, the Pitch and TAR are jointly estimated however, in alternative embodiments the pitch (periodicity) estimation may use any suitable periodicity technique, such as autocorrelation, cepstrum analysis or wavelets etc, and work directly on the digitized audio signal data rather than on the TAR.

(i) Descriptive Statistics from the Pitch Time Series:

Pitch values computed from episode "j" can be considered as a pitch-time series $\{p_j(k)\}$. Descriptive statistics of the $p_j(k)$ are used as a parameter in the snore-based model as follows:

| | |
|---|---|
| $meP_j$: | mean of $p_j(k)$, |
| $moP_j$: | mode of $p_j(k)$, |
| $varP_j$: | Variance of $p_j(k)$, |
| $sqP_j$: | Skewness of $p_j(k)$, |
| $kuP_j$: | Kurtosis of $p_j(k)$, |

These parameters shall be referred to as Pitch parameters in the remainder of this document.

ii) Parameterization of the Total Airways Response (TAR):

In order to quantify the shape of the TAR three different methods were employed.

Figure 2:
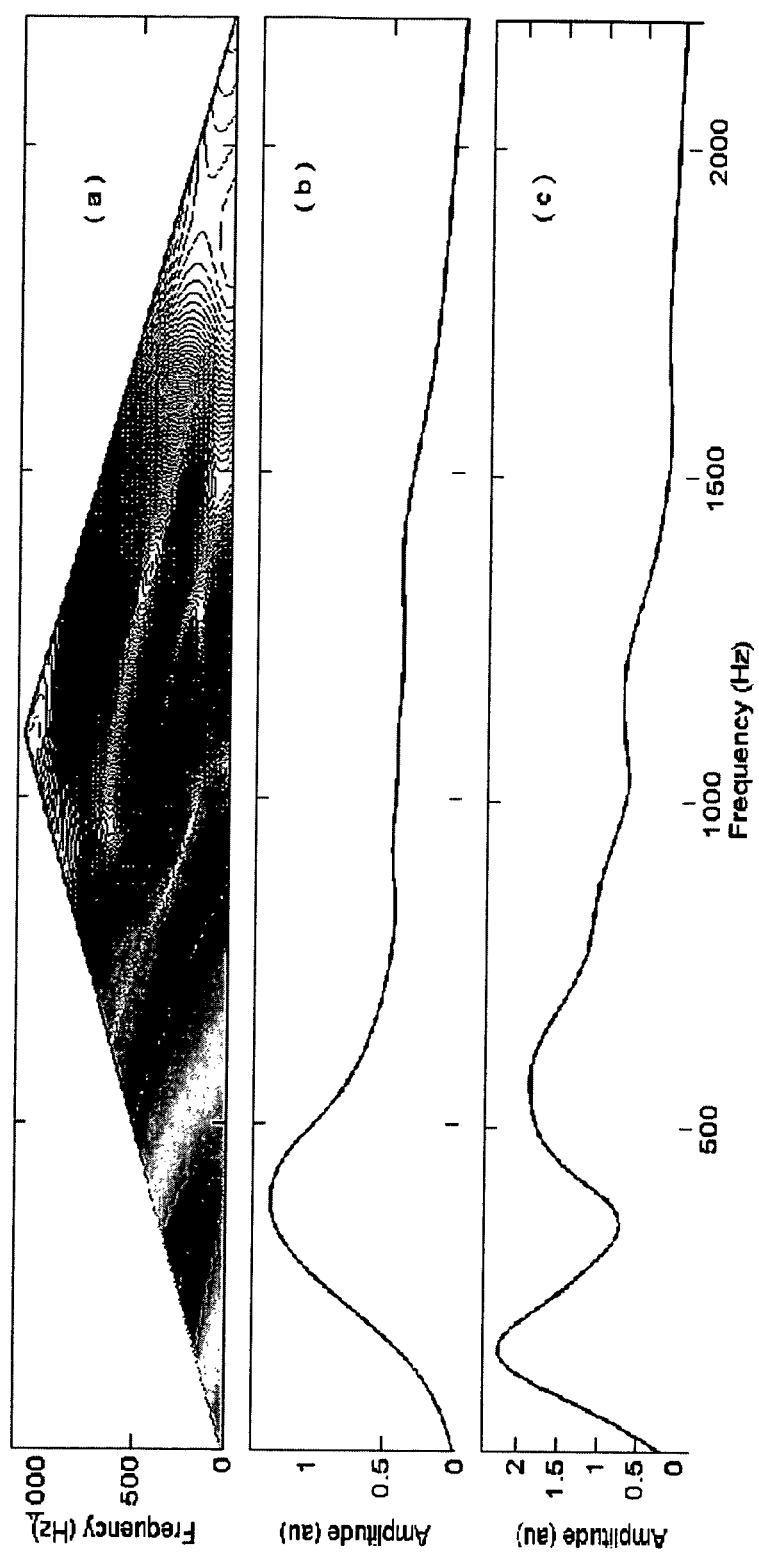
FIG. 2 (a) illustrates the Principal triangle of Bispectrum $PT(f_1, f_2)$.

In the first two methods the bispectrum $C_k(f_1, f_2)$ of the TAR (See Appendix B for details) of $k^{th}$ voiced snore segment within the snore episode j, were estimated. The sum of magnitude $B_k(f_n)$ (FIG. 2 *b*) was estimated in the principal domain inner triangle of the bispectrum, $PT_k(F_1, f_2)$ (FIG. 2 *a*) and the diagonal slice $D_k(f_n)$ (FIG. 2 *c*). $B_k(f_n)$ was estimated as;

$$B_k(f_1) = \sum_{f_2=1}^{N} |PT_k(f_1, f_2)| = B_k(f_n) \quad (2)$$

and DA/0 as $$D_k(f_n) = C_k(f_n, f_n) \quad (3).$$

Since $B_k(f_n)$ and $D_k(f_n)$ are one dimensional distributions of amplitude as function of frequency representing the spectral content of TAR the following parameters were estimated from them Centre frequency $Fc_k$ as;

$$Fc_k = \frac{\sum_{n=1}^{N} f_n * X_k(f_n)}{\sum_{n=1}^{N} X_k(f_n)} \quad (4)$$

Standard Deviation of frequency $Fd_k$ as;

$$Fd_k = \sqrt{\frac{\sum_{n=1}^{N} f_n^2 * X_k(f_n)}{\sum_{n=1}^{N} X_k(f_n)}} \quad (5)$$

Symmetry coefficient $Fs_k$ as;

$$Fs_k = \left| \frac{\sum_{n=1}^{N} f_n^3 * X_k(f_n)}{\sum_{n=1}^{N} X_k(f_n)} \right|^{1/3} \quad (6)$$

Ratio of total band amplitude for a given frequency band 'b' to total amplitude $Rb_k$ as;

$$Rb_k = \frac{\sum_{n=1}^{fb} X_k(f_n)}{\sum_{n=1}^{N} X_k(f_n)} \quad (7)$$

Ratio of total band amplitude for a given frequency band 'b' to total amplitude outside that band $ROb_k$ as;

$$ROb_k = \frac{\sum_{n=1}^{fb} X_k(f_n)}{\sum_{n=fb+1}^{N} X_k(f_n)} \quad (8)$$

where $X_k(f_n)$ represents $B_k(f_n)$ and $D_k(f_n)$ and n=1:N number of frequency bins in $B_k(f_n)$ and $D_k(f_n)$. Three values 500, 800 and 1000 were used for frequency bands "b" to estimate $R500_k$, $R800_k$, $R1000_k$, $RO500_k$, $RO800_k$ and $RO1000_k$.

For the $j^{th}$ snore episode, similar to pitch-time series $\{p_j(k)\}$, 18 time series represent the TAR. From each of these time series the mean and variance were estimated. In the rest of this document these parameters are referred to as Bispectral (BS) parameters and Diagonal slice (DS) parameters respectively. While the use of bispectral parameters is preferred and discussed in detail herein, any higher-order spectrum, i.e. order greater than 2, might be employed. For example, trispectrum parameters might be used instead of the bispectrum parameters. Similarly, while it is preferred that diagonal slice parameters be used, any slice except for one w parallel to w1=0, w2=0 or w1+w2=0 in the (w1, w2) plane can be used. The diagonal slice makes use of the (w1, w1) slice.

It is known that the human auditory system is able to hear linearly spaced tones below 1 kHz and logarithmically spaced tones above 1 kHz. Motivated by this observation, Mel-Frequency Cepstral Coefficients have been used in speech recognition applications. The inventors, wishing to provide a method for recognizing the OSAHS patients from snore sounds, estimated the Mel-Frequency Cepstral Coefficients of the TAR (MFCC Parameters) as the next set of parameters. Thirteen Cepstral coefficients ($MFCC1_j, \ldots, MFCC13_j$) were estimated using a triangular Mel-filter bank. While it is preferred that mel-frequency cepstral coefficients be used, in general other cepstral coefficients may also be used to implement less preferred embodiments of the invention.

D. Classification Model

A model using snore parameters, capable of classifying the two groups of snorers, subjects with low AHI (<10) and subjects with OSAHS, was now derived. To this end, there was now a pool of independent variables and one dependent variable with categorical outcomes, namely OSAHS and the non-OSASH snorers.

Logistic Regression analysis (LRA) and Linear Discriminant analysis (LDA) are two of the most widely-used statistical methods for analysing categorical dependent variables. To develop linear classification models, both these methods are appropriate. However, LDA has been developed for normally-distributed independent variables. Also, during the LDA, it is necessary to assume that the underlying data is either linearly related, or have equal within-group variances. On the other hand, LRA makes no assumptions about the distribution of the independent variables. It is reported in the literature that even though LDA and LRA have similar results when the normality assumptions are not violated, LDA is not suitable for all other cases (Pohar et al. 2004). Hence, it is assumed that LRA is a more flexible and more robust method in the case of violations of these assumptions.

LRA is the standard method frequently used for clinical classification problems[13, 14, 15]. Also because it was not feasible to check continually for the normality of the independent variable data and the relative ease of interpreting the results; LRA was settled on to classify the two groups.

In the following discussion, the dependent variable Y is assumed to be equal to "one" (Y=1) in subjects with OSAHS and "zero" (Y=0) in snorers with low AHI (<10).

A model was derived using logistic regression to estimate the probability Y=1 given the independent variables as follows;

$$P_l(Y = 1 | x_{1l}, x_{2l}, \ldots x_{Ml}) = \frac{\exp(\beta_0 + \beta_1 x_l + \ldots + \beta_M x_{Ml})}{1 + \exp(\beta_0 + \beta_1 x_{1l} + \ldots + \beta_M x_{Ml})} \quad (9)$$

where l (l=1, 2, ... L) is the observation number and M is the number of independent variables from $l^h$ observation in the model. $\beta_m$ (m=0, 1, ... M) are the model parameters estimated by the maximum likelihood method.

Snore parameters of 10 snores from each subject were averaged to derive independent variables $x_{ml}$ for regression model estimation. This resulted in maximum of 10 observations (L<=10) from each patient being used to derive the model.

The statistical software package SYSTAT 12® was used to carryout logistic regression analysis. The package allows the option of entering all available (M) independent variables corresponding to L observations and carryout stepwise analysis. The final model will include only the best independent variables that facilitate the classification.

The final model is then used to estimate the probability $P_l$ for L observations and each observation is classified as belonging to any one of the two groups using a probability threshold $P_{th}$. The $l^{th}$ observation is classified as OSAHS positive if $P_l > P_{th}$. Next each subject is classified in to the group where a majority of its observations fall into.

Model Validation

The general and simple approach for robust clinical validation of a classification model is to use the holdout method, where the available data are split into two sets, one to train the classifier and the other to test it. However holdout method of validation was not adopted in this study due to two reasons. The first being the sparse nature of the data sample (Table 1) and the other, the possibility of an unfortunate split where the error would be a maximum. The best validation method to suit the available data set was K-fold cross validation where each subject to be classified was left out from the training data set.

If the set of observations from $r^{th}$ patient $X_r=\{x_{ml}; l=1, 2, \ldots L\}$ and $r=1, 2, \ldots 41$ (number of subjects in the database). The following steps describe the validation process;

1. Split the data base into training and testing data sets such that Training data set, $X_{training}=X_r$, $r\neq a$ (a=1) and Testing data set $X_{testing}=X_r$, $r=a$.
2. Derive the model parameters and classify the subject in the testing data set
3. Repeat steps 1 and 2 varying a from 2 to 41
4. Generate the ROC curves using the results and estimate the performance parameters This method also makes it possible to use most of the available data in both model derivation and validation process.

Model Performance Evaluation

In a diagnostic test using any classification model, there are four possible outcomes with respect to the reference standard classification. They are: True Positive (TP), True Negative (TN), False Positive (FP), False Negative (FN). From these outcomes the measures of classification performance, Sensitivity, Specificity and Accuracy are estimated.

It is possible to obtain maximum sensitivity and specificity in classification of subjects by changing the probability threshold $P_{th}$ until an optimal $P_{th}$ is reached. In order to find this optimal $P_{th}$, the Receiver Operating Characteristic (ROC) curves were plotted by estimating sensitivity and specificity values for possible $P_{th}$ values ($0<P_{th}<1$ in steps of 0.01). As a measure of classification power of the model, the Area Under the Curve (AUC), was also estimated.

Three possible $P_{th}$ values were considered, corresponding to different model performance points in the ROC curve as follows:

$P_{th1}$—The $P_{th}$ at optimal model performance point in ROC curve (point with shortest distance to 100% sensitivity and 100% specificity performance)

$P_{th2}$—The $P_{th}$ at 100% sensitivity (with maximum specificity) model performance point in ROC curve $P_{th3}$—The $P_{th}$ at 100% specificity (with maximum sensitivity) model performance point in ROC curve.

We also estimated the Positive Predictive Value (PPV) and the Negative Predictive Value (NPV). PPV and NPV would provide insights to how the model would perform in a clinical application.

VIII. MODELING

Results & Discussion

A. Model Derivation

Using the methods described in section VI four different models P1, P2, P3 & P4 were derived from Pitch parameters, BS parameters, MFCC parameters and DS parameters respectively. FIG. 3 shows the ROC curves for these four models. As can be seen from FIG. 3 none of the models had good performance and therefore in the next stage models using combinations of parameter groups were derived. Even though Multi-Parametric models were derived for all possible combinations of the four groups, three Multi-Parametric models were selected to demonstrate how performance improves when the number of parameter groups are increased.

The three models, the parameter groups used to derive them and their performance are shown in the Table 2 and their ROC curves are shown in FIG. 4.

TABLE 2

Multi-parametric Models and their performance

| Model | PP | BSP | DSP | MFP | Sensitivity (Specificity) % | AUC | Acc. | PPV | NPV |
|---|---|---|---|---|---|---|---|---|---|
| A |   |   | ✓ | ✓ | 89.29(92.31) | 0.971 | 0.90 | 0.96 | 0.80 |
| B | ✓ |   | ✓ | ✓ | 96.43(92.31) | 0.984 | 0.95 | 0.96 | 0.92 |
| C | ✓ | ✓ | ✓ | ✓ | 96.43(100) | 0.995 | 0.98 | 1 | 0.93 |

PP—Pitch parameters, BSP—BS parameters, DSP—DS parameters, MFP—MFCC parameters, AUC Area Under the ROC Curve, Acc.—Accuracy, PPV—Positive Predictive Value, NPV—Negative Predictive Value It is evident from FIGS. 3 & 4 that the performance of the Multi-Parametric models are better than individual parameter models. From table II and FIG. 4 it can be observed that as the number of parameter groups is increased, the model performance increases. The best performance was observed in model C comprising of two independent variables from Pitch parameters (meP$_j$, sqP$_j$), two from BS parameters (me RO800j, varRO1000j), four from MFCC parameters (MFCC1$_j$, MFCC8$_j$, MFCC10$_j$, MFCC11$_j$) and three from DS parameters (meFc$_j$, meR1000$_j$, meRO800$_j$).

A. Model Validation

K-fold cross validation process was carried out to evaluate model. C. The classification performance was evaluated for each subject using a model, where the parameters βm have been derived by excluding all SE data of that subject. As stated in section VI, the performance of the model was evaluated at three different $P_{th}$ values. The Table 3 shows the performance of the model and the validation process at each of these $P_{th}$ values. The corresponding ROC curve for leave-one-out validation is shown in FIG. 5.

TABLE 3

Model performance evaluation results

|  | $P_{th}$ | AUC | Sensitivity % | Specificity % | Accuracy | PPV | NPV |
|---|---|---|---|---|---|---|---|
| Model | Pth1 | 0.85 | 0.995 | 96.43 | 100 | 0.98 | 1 | 0.93 |
|  | Pth2 | 0.7 |  | 100 | 84.62 | 0.95 | 0.93 | 1 |
|  | Pth3 | 0.85 |  | 96.43 | 100 | 0.98 | 1 | 0.93 |
| Validation | Pth1 | 0.85 | 0.967 | 89.29 | 92.31 | 0.90 | 0.96 | 0.80 |
|  | Pth2 | 0.7 |  | 96.43 | 76.92 | 0.90 | 0.90 | 0.91 |

TABLE 3-continued

Model performance evaluation results

| | $P_{th}$ | AUC | Sensitivity % | Specificity % | Accuracy | PPV | NPV |
|---|---|---|---|---|---|---|---|
| Pth 3 | 0.85 | | 89.29 | 92.31 | 0.90 | 0.96 | 0.80 |

AUC Area Under the ROC Curve, PPV—Positive Predictive Value, NPV—Negative Predictive Value

V. IMPLEMENTATION

Referring now to FIG. 6, there is depicted a computational device in the form of a personal computer system 52. Computer system 52 operates as an OSAHS diagnosis system according to a preferred embodiment of the present invention while executing an OSAHS diagnosis computer program which will be described shortly. Personal Computer system 52 includes data entry devices in the form of pointing device 60 and keyboard 58 and a data output device in the form of display 56. The data entry and output devices are coupled to a processing box 54 which includes a central processing unit 70.

Central processing unit (CPU) 70 interfaces with storage devices that are readable by machine and which tangibly embody programs of instructions that are executable by the CPU. These storage devices include RAM 62, ROM 64 and secondary storage devices i.e. a magnetic hard disk 66 and optical disk reader 48, via mainboard 68. The personal computer system also includes a USB port 50 for communication with an external ADC module 51 which pre-amplifies, filters and digitises signals from microphones 53 and 55. The microphones pick up sleeping sounds from a subject 42 lying on bed 40. The microphones do not touch the subject. In some circumstances one microphone may touch the bed to capture bed noise. Furthermore, one of the microphones may be a directional microphone that is used to measure background noise so that cars, barking dogs etc can be cancelled out of the digitized audio signal of the sleeping subject that is to be processed, via standard signal processing techniques.

Secondary storage device 66 is a magnetic data storage medium that bears tangible instructions, for execution by central processor 70. These instructions will typically have been installed from an installation disk such as optical disk 46 although they might also be provided in a memory integrated circuit or via a computer network from a remote server installation. The instructions constitute a software product 72 that is loaded into the electronic memory of RAM 62. When executed the instructions cause computer system 52 to operate as an OSAHS diagnosis system and in particular to implement an OSAHS diagnosis method that will be described shortly with reference to the flowchart of FIG. 7.

It will be realised by those skilled in the art that the programming of software product 72 is straightforward in light of the method of the present invention, a preferred embodiment of which will now be described. In the following method various variables are manipulated. It will be realised that during operation of computer system 52 to implement the method corresponding registers of CPU 70 will be incremented and data written to and retrieved from secondary storage 66 and RANI 62 by virtue of electrical signals travelling along conductive busses etched on mainboard 68. Consequently, physical effects and transformations occur within computer system 52 as it executes software 72 to implement the method that will now be described.

With reference to FIG. 7, a method according to preferred embodiment of the present invention will now be described. Initially at box 98 the subject's snore related digital sound file is received. At box 100 the subject's snore related sound, digital sound file is segmented into 100 ms segments which are classified as voiced snoring, unvoiced non-silence and silence using the automated SRS data segmentation method described in [12]. It will be realised that longer or shorter segments might be used and that 100 ms is simply a preferred segment duration. At the same time the sounds data file is processed at box 111 to generate a non-Gaussianity Index (NGI), which is an additional parameter for diagnosing OSAHS, which the inventors have developed and which will be described later in this specification. At box 102 the Pitch and TAR of each segment, that was identified as a voiced snoring segment, is estimated using the Higher Orders Statistics (HOS) procedure described in [11].

At box 104 the mean pitch $meP_j$ and the Skewness of the pitch values $sqP_j$ is calculated as discussed in paragraph D.(i) above. At box 106 the Bispectrum Parameters (BS) mean of $RO_{800}$ and the variance of $RO_{1000}$ are calculated as discussed in D.(ii) above. At box 108 the Diagonal Slice parameters (DS) being the mean of the center frequency $Fc_k$, variance of $R_{1000}$ and mean of $R_{800}$ are calculated as discussed in D. (ii) above.

At box 110 the $1^{st}$, $8^{th}$, $10^{th}$ and $11^{th}$ coefficients of the Mel-Frequency Cepstral Coefficients (MFCC) are calculated.

At box 112 the parameter values that have been calculated in boxes 104, 106, 108, 110 and 111 are applied to the pre-calculated obstructive sleep apnea (OSAHS) model. The OSAHS model is the logistic regression model discussed in section E. above. That model uses model parameters derived from training data gathered from subjects suffering from either simple snoring or OSA. Other classification models may also be suitable. For example although less preferred, discriminant analysis may be used. Alternatively a decision machine such as a Support Vector Machine might also be used to classify the calculated parameters as either being associated with a subject suffering from OSAHS or not.

Application of the calculated parameters to the model at box 112 results in a probability value being returned. At box 114, if the probability value is greater than or equal to a predetermined threshold then the subject is deemed to be suffering from OSAHS and a corresponding message is displayed, for example on display 56 (FIG. 6). Alternatively, if the probability value that is returned by the model is less than the predetermined threshold value then at box 116 an "OSA is not indicated" type of message is displayed.

As an alternative to the embodiment shown in FIG. 6, a dedicated apparatus for diagnosing a sleeping disorder in a subject may be provided according to further embodiment of the invention a block diagram of which is provided in FIG. 7A. The dedicated apparatus includes a microphone port 121 for connection of a microphone 120. The microphone port 121 is coupled to an analog to digital converter 122 which produces a digital audio signal that is passed to a digital signal input point 123 that in turn provides a digitized audio signal to the data logger 124. The data logger 124 serves to record data entering, and generated by the apparatus and also to cache the digital audio signal. It will be realised that a pre-recorded digital audio signal might be applied to digital audio input point 123 thereby bypassing microphone 120 and ADC 122. A segmentation module 126 is coupled to the data logger and provides segments of the digitized audio signal to the Snore Segment Identifier 128, which in turn is arranged to classify segments as voiced snoring, unvoiced non-silence and silence. A total airways response (TAR) calculator 130, pitch calculator 132 and MFCC calculator 134 are each coupled to an output side of the snore segment identifier module 128. Each of these modules is respectively arranged to calculate pitch, bispectrum, diagonal slice and MFCC parameters for the snore segments received from the snore segment identifier 128 and to output electrical signals to bus 145 corresponding to the calculated parameter values. Similarly, the NGI calculator produces a non-Gaussianity index for the digitized audio signal. A suitable data bus 145 is provided to convey output signals representing the calculated parameters from modules 130, 132, 134 and 136 to classification module 144. The classification module 144 is arranged to process the calculated parameters and compare a resulting diagnosis probability to a predetermined threshold value. The results of this comparison are then indicated on video display 142, which communicates with the classification module 133 via display controller 140 and bus 145. For example, if the results of the comparison are over threshold then display 142 may be driven to indicate "OSAHS is present". The display 142 also presents auxiliary information such as the loudness and duration of detected snores.

A user control interface 138 is provided to allow an operator to vary parameters of the various modules as indicated by the dashed lines in FIG. 7A. For example, the operator may wish to vary the cut-off frequency of the pre-emphasis module 127, in which case adjustment may be made via control interface 138. Similarly, operator may wish to input a selection between different threshold values for classification in the classification module 144. These different threshold values will have been predetermined to maximise the negative predictive value (NPV) or positive predictive value (PPV) to suit the operators requirements, e.g. to screen in or screen out for OSAHS. The Data Logger 124 may also be controlled by the control interface so that the operator can have it record data passing along bus 145, such as the results from the various calculator modules 130-136.

The display controller 140 and display 142 are also arranged to

Other alternatives are also possible. For example, a low cost audio record-only device may be located near the subject 42. Upon sufficient audio having been recorded from the subject the audio data may then be transferred to a remotely located facility for processing according to the previously described method. Another alternative is to provided a miniature wearable microphone-based device, for example with Bluetooth connectivity to a recorder or a transmission device. In this regard a cellular phone may be a convenient way of transmitting the audio data to the remote facility for processing.

Embodiments of the present invention may be used in conjunction with facility-based diagnosis of OSA. For instance, in combination with an EEG channel to measure the neural dimension of OSA, while the snore sounds capture the mechanical/respiratory features of OSA. A much simpler device, which would operate on less than five subject data channels for example, would then be possible as opposed to the current in-facility equipment that often makes use of more than fifteen channels. In addition such an EEG+Snore system might be fully automated thereby removing the need for manual analysis of the signals.

IX. A NON-GAUSSIAN INDEX MODEL

Previously, with reference to box 111 of FIG. 7 and with reference to box 136 of FIG. 7A, reference has been made to the calculation of another parameter, ie. a Gaussianity distribution parameter in the form of a non-Gaussianity distribution index, that may be used in embodiments of the invention to assist in diagnosis of sleep dysfunction such as OSAHS.

The inventors have hypothesized that snore sounds are non-Gaussian signals, i.e. they do not exhibit a Gaussian distribution, and have conceived of a non-Gaussianity Index (NGI) for the diagnosis of OSAHS via measuring the amount of deviation of snore data from Gaussianity. Accordingly FIG. 8 is a flowchart of a method according to a further embodiment of the present invention which involves the computation of NGI. This method is programmed as tangible instructions on a machine readable media, for example a magnetic or optical disk, or Solid State Disk, for execution by one or more processors of a suitable hardware system such as that of FIG. 6.

By way of explanation, the method has been developed by initially modeling the $k^{th}$ segment $\tilde{x}_{jk}[n]$ of a digitized overnight Snore Related Sound (SRS) signal, $\tilde{X}_j$, recorded from the $j^{th}$ arbitrary subject, as:

$$\tilde{x}_{jk}[n]=\tilde{s}_{jk}[n]+\tilde{b}_{jk}[n], \quad (10)$$

$\tilde{s}_{jk}[n]$ is the true SRS signal of interest, and $\tilde{b}_{jk}[n]$ represents noise and background sounds unrelated to the SRS. The index n=1, 2 N is the sample number within the segment k, and, N denotes the total length of the segment in number of samples. Note that the overall recording $\tilde{X}_j$ of the patient j can then be expressed as the concatenation of non-overlapping segments as $\tilde{X}_j=\{\tilde{x}_{j1}[n]|\tilde{x}_{j2}[n]| \ldots |\tilde{x}_{jk}[n]| \ldots |\tilde{x}_{jK}[n]\}$, where k=1, 2 ... K indicates the segment number, and K is the total number of segments in the overnight recording.

$\tilde{b}_{jk}[n]$ is modeled as the combination of Gaussian and non-Gaussian components. The Gaussian component mainly consists of the electronic noise contributed by the instrumentation. The non-Gaussian component, however, is other background sounds such as speech and movement related sounds. The desired signal, $\tilde{s}_{jk}[n]$, constitutes of three components [20], i.e. Pure Breathing Episodes (PBE), Snoring Episodes (SNE) and inter-episode silence, which have been previously defined.

Both PBE and SNE episodes may include segments of intra-episode silence, mostly as a pause of breathing between inspiration and expiration cycles. By the above definition, SNEs require the presence of periodic structures within episodes, whereas PBEs require the absence of periodicity. Such periodic structures (voiced-components of snoring) tend to make the SNE data non-Gaussian. The noise-like non-periodic components in SNEs and PBEs are similar to unvoiced-components of speech. This is illustrated in the graph of FIG. 9.

Following the source/vocal-tract model in speech synthesis, the SRS synthesis process is modeled [36] as shown in FIG. 3, as a linear convolution between a function (TAR), representing the acoustical properties of the upper airways, and a source representing the original energy responsible for the sounds that are heard. If the segment k under consideration is a voiced-segment, the source function is a pulse-train corresponding to the characteristic vibratory sound of snoring; if the segment is unvoiced, the source function is a noise generator.

The approach taken is to quantify the deviation from Gaussianity of SRS data and use the resulting index as a measure for OSAHS severity.

A. SRS Pre-Processing

The SRS signal $\tilde{X}_j$ recorded at the microphone (box 200 of FIG. 8) is digitized by A/D converter 51 and pre-processed by CPU 70 at box 202 as described below, to improve and boost the energy of the higher frequency and voiced-components of the SRS signal. In the following described steps the data is further processed by the CPU 70 in accordance with the instructions stored in software product 72, said instructions being detailed in the boxes of the flowchart in FIG. 8.

The preprocessed $\tilde{X}_j$ will be denoted by $X_j$ and used in further processing as described below and in the flowchart of FIG. 8.

i) Pre-Emphasis Filtering:

A pre-emphasis filter is used to boost the overall energy of the SNEs and improving the signal-to-noise ratio at higher frequencies. The parameter α in equation (11) can be adjusted to set the filter to the desired cut-off frequency. Pre-emphasis filtering is carried out with α typically set to the range of 0.96 to 0.98.

$$x_{jk}[n] = \tilde{x}_{jk}[n] - \alpha \tilde{x}_{jk}[n-1] \quad (11)$$

ii) Background Noise and Interference Reduction:

The background noise ($\tilde{b}_{jk}[n]$) mainly consists of (electronic) instrumentation noise and unwanted sounds independent of $\tilde{s}_{jk}[n]$ (e.g. night-time speech, groaning, duvet noise etc.). As typically followed in the literature, the electronic noise is treated as a Gaussian process [21, 24]. The method described in this section is centered on computing the distance of the observations from a Gaussian distribution, and thus electronic noise theoretically does not affect the calculations. Furthermore, low-noise sound acquisition systems, like the one employed in the recording process, are now widely available, and the SNR can be further improved by filtering (e.g. pre-emphasis and low-pass). For these reasons the contribution of electronic noise to $\tilde{b}_{jk}[n]$ can be safely ignored.

Unwanted background sounds such as speech and groaning may be observed in an overnight snore recording made in the hospital. These sounds are highly concentrated in the first and last 30 minutes of the recording, when the patient is awake, and conversation between the patient and the attending medical technologist occurs. The first and last 30 minutes of data are removed (box 202 FIG. 8). This does not pose any difficulties for the method, as a typical snore recording is commonly 6-8 hours long, and also, snoring is not expected where the subject is awake. Sporadic events of duvet noise and groaning etc. may also be present during the night but they appear as relatively rare, isolated events. The statistical analysis that is proposed utilises long hours of continuous SRS data, and hence, such isolated events do not affect the results in any significant manner.

B. Calculating the Non-Gaussianity Score (NGS)

The pre-processed SRS signal, $X_j$, is used to derive a new segment per segment measure, called the Non-Gaussianity Score (NGS), which is a quantitative measure of the deviation from Gaussianity of a segment of $X_j$, $X_{jk}[n]$. The method is centered on computing the Normal Probability Plot [38].

(i) Normal Probability Plot for the Segment $x_{jk}[n]$:

The normal probability plot is a plot of the midpoint probability positions of a given data segment versus the theoretical quantiles of a normal distribution [24]. If the distribution of the data under consideration is normal, the plot will be linear. Other probability distributions will lead to plots that deviate from linearity, with the particular nature and amount of deviation depending on the actual distribution itself. The normal probability plot is often used as a powerful qualitative tool in visualising the 'Gaussianity' of a given set of data. A method is proposed to derive a quantitative measure for the deviation from Gaussianity, based on the normal probability plot of $x_{jk}[n]$.

To obtain the normal probability plot for a segment of the analysed SRS signal, $x_{jk}[n]$, the inverse of the normal Cumulative Distribution Function (γ) for the data is first calculated (at box 206 of FIG. 8) as follows:

$$\gamma = F^{-1}(p|\mu,\sigma) = \{\gamma : F(\gamma|\mu,\sigma) = p\} \quad (12)$$

where, $$p = F(\gamma|\mu,\sigma) = \frac{1}{\sigma\sqrt{(2\pi)}} \int_{-\infty}^{\gamma} \frac{-(t-\mu)^2}{2\sigma^2} dt^2 \quad (13)$$

μ=mean of the analysed segment $x_{jk}[n]$
σ=standard deviation of analysed segment $x_{jk}[n]$ The probabilities were then assigned to P in (13) to obtain the required γ values for plotting the normal probability plot of the data in $x_{jk}[n]$. However, the normal probability plot conducts a comparison between γ and probabilities of a would-be, or reference, Gaussian dataset, if $x_{jk}[n]$ was to represent a data segment with a Gaussian distribution. This is, thus, calculated (at box 208 of FIG. 8) and referred to as the probability set g in (14).

ii) A Quantitative Measure for the Non-Gaussianity of $x_{jk}[n]$ (NGS, $\psi_{jk}$):

The deviation of the probability plot of $x_{jk}[n]$ from a straight line (i.e. the shape of a true Gaussian probability plot, g) was chosen as the segmental measure of non-Gaussianity, symbolised by $\psi_{jk}$. Linear regression [21] was utilised to estimate $\psi_{jk}$ at box 210 of FIG. 8.

$$\psi_{jk} = 1 - \left( \frac{\sum_{n=1}^{N}(g[n]-\bar{g})^2}{\sum_{n=1}^{N}(\gamma[n]-\bar{\gamma})^2} \right) \quad (14)$$

Where, g[n] is the set containing probabilities of the reference normal data for segment $x_{jk}[n]$, and $\psi_{jk}$ is the non-Gaussianity score directly mapped to the segment $x_{jk}[n]$. It must be noted that due to use of linear regression the NGS values range such that, $(0 \leq \psi_{jk} \leq 1)$.

After estimating $\psi_{jk}$, for all k=1, 2 ... K (at box 210 of FIG. 8) the procedural steps (S1) to (S4) below were followed:

(S1) At box 210, the obtained NGS ($\psi_{jk}$) values are directly mapped to each analysed segment, $x_{jk}[n]$, as an obtained score representing all samples of the segment of data. These scores are referred to as $\psi_{jk}$, to indicate the non-Gaussianity score of the $k^{th}$ segment of the $j^{th}$ subject.

(S2) At box 212 the $\psi_{jk}$ values mapped to $x_{jk}[n]$ segments are thresholded using threshold value β. Define a new sequence $y_{jk}[n]$, n=1, 2 ... N and k=1, 2 ... K such that, for $\psi_{jk}$ values above β, all samples of defined segments, $y_{jk}[n]$, are set to "1" (at box 214) while otherwise they are set to "0" (at box 216).

$$y_{jk}[n] = \begin{cases} 1 & \text{if, } \psi_{jk} > \beta \\ 0 & \text{if, } \psi_{jk} \leq \beta \end{cases} \quad (15)$$

(S3) At box 218, once all $y_{jk}[n]$ segments are defined, the $X_j$ SRS signal is partitioned into larger blocks consisting of concatenated and non-overlapping $y_{jk}[n]$ segments, with each block having a length of Q segments and thus NQ samples, in order to obtain blocks $B_{jl}[m]$, where, l=1, 2 ...

$$\left\lfloor \frac{K}{Q} \right\rfloor$$

and m=1, 2 ... NQ. For simplicity, NQ, is referred to, which represents block length in number of samples, using L.

(S4) At box 220, the summation of the L samples within each $B_{j2}[m]$ block is then obtained as $$\sum_{m,\forall l} B_{jl}[m].$$

If this value is equal to or above "1", a new block $C_{jl}[m]$ is defined as $C_{jl}[m]=1$ for $l=1, 2 ...$ $$\left\lfloor \frac{K}{Q} \right\rfloor$$

and m=1, 2 ... L, otherwise, it is defined as $C_{jl}[m]=0$.

(S5) At box 226 the summation over all L samples for each $C_{jl}[m]$ was then obtained as $$\sum_{m,\forall l} C_{jl}[m]$$

and divided by the total length of the block, L, to achieve the total number of blocks within the $X_j$ signal defined as $C_{jl}[m]=1$. This value was then divided by the total length of the analysed $X_j$ signal, in hours, in order to obtain the overall non-Gaussianity Index (NGI), (equation 16) for the $j^{th}$ subject. This is referred to using symbol $\psi_j$, denoting the overall NGI of the $j^{th}$ subject, which is in turn utilised for diagnosis.

$$\psi_j = \frac{\left(\sum_{m,\forall l} C_{jl}[m]\right)}{(NQ)(\text{Length of } X_j \text{ in hours})} \quad (16)$$

At box 228 the NGI for the $j^{th}$ subject is displayed on monitor 56 (FIG. 6) for viewing by an operator. The NGI can then be taken into account when making a diagnosis of in relation to the subject. Alternatively, the NGI may be incorporated as a parameter of the model that was previously discussed in relation to FIGS. 6 and 7.

In particular, a non-contact, take-home non-Gaussianity apnea monitor incorporating the method may be provided in conjunction with the apparatus previously described in relation to FIGS. 6 and 7 or alternatively in stand alone format. Where the non-Gaussianity detection method is incorporated into the apparatus previously described in relation to FIGS. 6 and 7 then an additional step, or steps will be incorporated to calculate the non-gaussianity index and then subsequently at box 112 the non-Gaussianity index will also be applied to the pre-calculated OSAHS model.

X. NON-GAUSSIANITY INDEX METHOD

Results

This section provides descriptions of the database utilised for the evaluation process, the testing and training methods employed during evaluation, and the obtained evaluation results.

The Database

The AJaPSG (Australia-Japan PSG) [32] database was used for the work of this paper. It consisted of snore sounds recorded from 86 subjects while undergoing routine PSG tests at the Sleep Disorders Unit of The Princess Alexandra Hospital, Brisbane, Australia.

The sound acquisition system consisted of a pair of matched low noise microphones having a hypercardiod beam pattern (Model NT3, RODE, Sydney, Australia). The nominal distance from the microphone to the mouth of the patient was 50 cm, but could vary from 40 to 70 cm due to patient movements. A professional quality pre-amplifier and A/D converter unit (Model Mobile-Pre USB, M-Audio, California, USA) was used for data acquisition, at a sampling rate of 44.1 kHz and a 16 bits/sample resolution. The system had a 3 dB bandwidth of 20,800 Hz at 44.1 kHz.

PSG data were gathered from a Compumedics (Sydney, Australia) sleep acquisition system. PSG measurements consisted of standard channels such as EEG, FOG, ECG, EMG, leg movements, respiration nasal airflow, nasal pressure, respiratory movements, blood oxygen saturation, breathing sounds and the body position. Expert human scorers analysed PSG data and computed the AHI as part of the standard diagnostic protocol. The database consisted of subjects with AHI ranging from 0.5 to 106 (AHI mean=29.85, AHI standard deviation=25.74), and was divided into the two subsets of testing and training. The training set was selected by randomly choosing 20 of the 86 subjects in such a way as to achieve an approximately uniform distribution for the training set (see FIG. 11). The remaining subjects were then utilised for the testing process. It must be noted that the training and test sets were independent and mutually exclusive from one another. This division is shown in TABLE 4. In addition, the version of the AJaPSG database employed for evaluation purposes had a sampling rate downsampled to 16 kHz.

TABLE 4

The training and testing set divisions of the SRS database consisting of 86 subjects with a total of 22 non-OSAHS patients and 64 OSAHS patients

| Set Type | No. of Subjects | AHI Range | AHI < 10 | AHI ≥ 10 |
| --- | --- | --- | --- | --- |
| Training | 20 | 0.5-92.9 | 7 | 13 |
| Testing | 66 | 0.6-106.7 | 17 | 49 |
| Total | 86 | 0.5-106.7 | 22 | 64 |

Pre-Emphasis Filtering of $X_j$

In section IX the use of the pre-emphasis filter was discussed. The pre-emphasis filter is used to correct the roll-off observed in the spectrum of quasi-periodic signals such as snoring. This filter acts as a high pass filter, eliminating low frequency noise and, in turn, relatively boosting the energy of the higher frequency region of snore segments.

The response of the pre-emphasis filter is dependent on the parameter α, as was previously mentioned in section IX. This variable is commonly set between the range of 0.94 to 0.98, and little difference is observed between the values in this range. FIG. 12 displays the magnitude response (top row) and phase response (bottom row) of the pre-emphasis filter, respectively. FIG. 12 displays the response of the filter for five different α values.

A value of (α=0.96) was utilized to achieve a mid-point response between the commonly utilised values of 0.94 to 0.98. The results indicated that low frequency noise was attenuated and the energy of snore segments were boosted accordingly. An example of the effect of the pre-emphasis filter can be observed in FIG. 13.

Computation of the Non-Gaussian Score (NGS)

It was discussed (in section IX) that a normal probability measure was utilized to obtain the $\psi_{jk}$ scores for each analysed segment of data, $x_{jk}[n]$. The success of normal probability analysis relies on differentiating a normally distributed process from a non-normally distributed one. The energy-normalised distribution templates for a segment of data taken from a breathing/silence episode, snoring episode from a non-OSA, and snoring episode from an OSAHS patient, along with their corresponding normal probability plots and NGS scores can be seen respectively in FIGS. 14 (a), 14 (b), and 14 (c). The visual inspection of FIG. 14 indicated that the distribution of an analysed segment of snore data from an OSAHS subject is more non-Gaussian than that of a non-OSAHS subject, and in turn a segment of breathing or silence, which possesses a highly Gaussian distribution. This was the motivation behind the implementation of a feature capable of measuring deviation from Gaussianity. Hence, the normal probability plot was utilized and the method described in section IX was employed to obtain the NGS measure. FIG. 14, also displays the normal probability plots corresponding to the distribution shapes. In addition, it can be seen that the NGS measure provides great distinction between each of the categories of the analysed SRS segments.

D. Non-Gaussianity Index (NGI) and OSAHS Diagnosis

The system was first trained using the training set previously discussed in section III-A. The training set consisted of overnight snoring sounds (6-8 hours duration) recorded from 20 subjects. The 20 subjects were randomly and in such a way as to achieve an approximately uniform distribution with respect to their associated AHI. This was done to avoid biased experimentation. The remaining 66 subjects were then used as the test set.

(i) β Threshold Tuning:

Training was utilised to obtain an optimum β value for each L-length partitioning experiment. To do this, 10 different values were utilised for L. The L values were chosen in a such a way so as to correspond to: 1, 3, 5, 7, 9, 10, 15, 20, 25, and 30 seconds in length. This was done to mark $C_{jl}[m]$ blocks as "success" ($C_{jl}[m]$=1) or "failure" ($C_{jl}[m]$=0), as was displayed in FIG. 8. Typically a block length of 30 seconds is utilised in PSG studies to obtain the estimated apnea/hypopnea episodes and thus obtain AHI [22]. In this study, the 10 distinct L values were utilized to observe the possible effects of the block partitioning length on the detectability of the diagnostic system.

Receiver operating curves (ROC) were used to optimise the method. ROC curves were chosen to analyse the behavior of the system with respect to threshold variation. ROC curves were calculated for β values (range of 0 to 1 with steps of 0.01) per L-length partitioning experiment. Areas under each of the ROC curves were then plotted against their associated β values, those values that gave an area of 1 under the curve, or otherwise known as, a detectability of 100%, were marked. The median β value of the set, which gave the maximum area, was chosen to leave a guard-band for the error caused by the trained β value used for testing, thus ensuring error minimisation and increased detectability for the future testing process. FIG. 15 displays the 10 graphs for detectability versus β. Each graph displays the optimum β point and the L value utilized for the experiment.

ii) Evaluation Using Tuned β:

The obtained β values from the training process were then utilised to conduct testing. The testing of the system was only carried out on the chosen β value from the training set. Hence, only one ROC curve was obtained per L-length partitioning experiment. It must be noted that testing experiments were conducted independently to the training experiments. That is, the training set was analysed using the ROC curves to obtain the optimum threshold for that set only. This value was then employed to test the testing set and achieve the reported results. Only the β values were chosen using information obtained from the training data. The obtained ROC curves for each of the L-length partitioning experiments can be seen in FIG. 16.

E. Optimisation and Diagnosis

FIG. 16 displays the ROC curves for the testing data set. The threshold utilised to conduct the diagnosis at the set β value was varied to obtain the displayed ROC curves. This threshold value corresponded to the overall non-Gaussianity index, $\psi_j$, and was calculated using (7). To do this, 100 points were chosen between the indices obtained for the lowest AHI and the highest AHI patients. The sensitivity and specificity values were then obtained at each index value in order to obtain the index equivalent to an AHI of 10 (which is utilised to separate OSAHS and non-OSAHS patients). This allowed for optimisation based on positive predictive value (ppv) and negative predictive value (npv) measures. The ppv measure indicates the proportion of subjects with OSAHS who are correctly diagnosed. The npv measure, on the other hand, is a measure of the proportion of subjects that are non-OSAHS subjects and are correctly diagnosed. Finally, it is seen that detectability values of over 96% were achieved for the diagnosis of the 66 test patients. In addition, the optimum point was marked on each ROC curve for each L-length partitioning experiment.

i) Effect of L in Optimization:

It is seen from FIG. 16, that utilising a value of L, that corresponded to a block length of 25 seconds, to partition the $X_j$ signal into $B_{jl}[m]$ blocks produced the most accurate results, but was virtually no different to the results obtained using any other length of L. Hence, little difference was found between the results obtained from the 10 L-length partitioning experiments based on the detectability measure, with the least accurate L-length partitioning being the L corresponding to 1 s blocks. Even in this case, a difference of just over 1% was observed between the accuracy of L corresponding to 25 s and 1 s. It must be noted that different L values would provide different index values employed for diagnosis. For L corresponding to 25 s a normalized index range of 0 to 144 can be achieved. These values represent an average count of the number of ($C_{jl}[m]$=1) blocks observed per hour during the $X_j$ recording. This is a range similar to the AHI range of 0 to 120 counts per hour, which is achieved using L corresponding to 30 s. Hence, the NGI has the potential to represent AHI using similar values.

ii) Analysis of Optimized Results:

The L-length partitioning experiment at L corresponding to 25 s was analysed in detail to obtain further information. FIG. 17 displays the 86 points representing the 86 subjects, with the NGI graphed against the original AHI values of the subjects. The error regions have been marked. It can be seen that, when an AHI=10 is employed as the diagnostic boundary, only 5 of the subjects fall into the False Negative (FN)

region, while no False Positives exist. Hence, it can be said that the non-Gaussianity index (NGI) can be utilised to screen or diagnose OSAHS subjects from non-OSAHS. The NGI, corresponding to diagnosis using an AHI of 10, marks OSAHS subjects as ($\psi_{thresh} \geq 15.44$) and non-OSAHS subjects as ($\psi_{thresh} < 15.44$) with a detectability accuracy of 97.34%. The results of the testing and training experiments are summarised and displayed in TABLE 5, 6, and 7.

TABLE 5

Training data details for 10 L-length training sets.

| L | Optimum β | Detectability (A %) |
|---|---|---|
| 1 | 0.20 | 100 |
| 3 | 0.27 | 100 |
| 5 | 0.32 | 100 |
| 7 | 0.33 | 100 |
| 9 | 0.34 | 100 |
| 10 | 0.34 | 100 |
| 15 | 0.36 | 100 |
| 20 | 0.34 | 100 |
| 25 | 0.36 | 100 |
| 30 | 0.37 | 100 |

Each L value was trained using 20 of the 86 subjects.
The optimum β was set based on the highest detectability achieved

TABLE 6

Testing data for L-length test sets.

| L | β Value | Maximum Detectability (A %) | Diagnostic NGI threshold ($\Psi_\downarrow$ thresh) |
|---|---|---|---|
| 1 | 0.20 | 96.18 | 61.54 |
| 3 | 0.27 | 96.84 | 35.30 |
| 5 | 0.32 | 96.68 | 26.26 |
| 7 | 0.33 | 96.68 | 23.69 |
| 9 | 0.34 | 96.84 | 21.53 |
| 10 | 0.34 | 96.84 | 20.04 |
| 15 | 0.36 | 97.18 | 16.60 |
| 20 | 0.34 | 97.18 | 16.29 |
| 25 | 0.36 | 97.34 | 15.44 |
| 30 | 0.37 | 97.18 | 14.22 |

NGI threshold is displayed for L length partitioning with the optimum (L = 25 s) giving a detectability measure of 97.34%

TABLE 7

The test results and detectability values obtained for diagnostic AHI values of 5, 10, 15 and 30.

| AHI | L | β Value | Maximum Detectability (A %) | Diagnostic NGI threshold ($\Psi_\downarrow$ thresh) |
|---|---|---|---|---|
| 5 | 25 | 0.54 | 92.00 | 7.61 |
| 10 | 25 | 0.36 | 97.34 | 15.44 |
| 15 | 30 | 0.21 | 96.67 | 32.98 |
| 30 | 30 | 0.15 | 86.30 | 58.00 |

It can be seen that the NGI may be tuned to obtain optimum results at various AHI values.

As was seen in section III-E, the training data was utilised to obtain threshold values β and $\psi_{thresh}$ for performing testing and evaluation based on specific error optimisations. Hence, experiments were carried out to analyse the performance of NGI when optimised for ppv or npv measures. The results were obtained and can be observed in TABLE V and VI. The tables indicate that the most accurate diagnosis, in either case, is obtained for NGI value corresponding to (AHI=10). In addition, the system performs at a higher specificity when optimised for the ppv measure, and a higher sensitivity when optimised for the npv measure.

TABLE 8

The table displays ppv, npv, sensitivity, and specificity for the four diagnostic AHI values based on optimised ppv value

| AHI | PPV | NPV | Sensitivity % | Specificity % |
|---|---|---|---|---|
| 5 | 1 | 0.476 | 91.11 | 80.00 |
| 10 | 1 | 0.815 | 93.02 | 100.00 |
| 15 | 0.964 | 0.825 | 91.43 | 93.33 |
| 30 | 0.864 | 0.828 | 76.92 | 79.17 |

TABLE 9

The table displays ppv, npv, sensitivity, and specificity for the four diagnostic AHI values based on optimized npv values

| AHI | PPV | NPV | Sensitivity % | Specificity % |
|---|---|---|---|---|
| 5 | 0.974 | 0.769 | 96.21 | 83.33 |
| 10 | 0.941 | 0.957 | 98.46 | 84.61 |
| 15 | 0.931 | 0.917 | 94.64 | 89.18 |
| 30 | 0.808 | 0.906 | 88.37 | 84.21 |

APPENDIX A

The theoretical derivation of HOS based algorithm for joint estimation of pitch and TAR from the SRS signals. The third order cumulants [14] $c_s(\tau,\rho)$ of the zero mean observation s(n) in equation (1) is defined as:

$$c_s(\tau,\rho) = E\{s(n)s(n+\tau)s(n+\rho)\}, \quad (17)$$

where $E\{.\}$ denotes the expectation operator.

The bispectrum $C_s(\omega_1,\omega_2)$ [15] of s(n) is defined to be the Fourier transform of the third order cumulant $C_s(\tau, \rho)$. Converting (10) to the bispectrum domain the following result is obtained:

$$C_s(\omega_1,\omega_2) = C_x(\omega_1,\omega_2)H(\omega_1)H(\omega_2)H^*(\omega_1,\omega_2), \quad (18)$$

where $C_x(\omega_1,\omega_2)$ is the bispectrum of x(n), $H(\omega)$ is the spectrum of h(n), "•" denotes conjugate Now the problems at hand are to estimate (i) the TAR (h(n)), and (ii) the properties of the source excitation x(n) as relevant to the voiced and unvoiced snore segments.

In this document the bicepstrum [14], [15] is used, which is defined as the 2-dimensional cepstrum of the bispectrum. In the bicepstrum domain, from (11) the following result is obtained, $$b_s(m_1,m_2) = b_x(m_1,m_2) + b_h(m_1,m_2), \quad (19)$$

where $b_x(m_1,m_2)$, $b_h(m_1,m_2)$ and $b_s(m_1,m_2)$ are the bicepstra of x(n), h(n) and s(n) respectively. Note that the multiplication in the bispectra domain has now become addition in the biceptra domain.

As known in the HOS signal processing community [14], [15], the slice $b_s(m,0)$ of the bicepstra $b_s(m_1, m_2)$ gives the 1-dimensional complex cepstrum of s(n), which can be used to reconstruct the signal s(n) or extract x(n) and h(n) through inverse 1-dimensional complex cepstra operations.

As described in section III B when the "source excitation" x(n) for voiced snoring is considered to be a pseudo-periodic pulse-train, the 1-dimensional complex cepstrum $b_x(m,0)$ of x(n) too consists of a periodic impulse train. The contribution $b_h(m,0)$ of h(n) to the complex cepstrum $b_s(m,0)$ of s(n) is non-periodic and can be easily separated from $b_s(m,0)$, through an appropriate window operation as defined by:

$$W(m; l) = \begin{cases} 1, & \text{for } -1 < m < l \\ 0, & \text{otherwise} \end{cases} \quad (20)$$

The symbol W(m;l) represents a rectangular window with its size parameterized by l. If the first occurrence of the repetitive, impulse peak of $b_s(m,0)$ is noted at the sample number m=L (corresponding to the pitch), one can set l=L−1 in (13). Applying W(m;l) to $b_s(m,0)$ we get, $$b_{sw}(m,0) = b_{hw}(m,0) = b_h(m,0), \quad (21)$$

where $b_{sw}(m,0)$ and $b_{hw}(m,0)$ are the windowed versions of $b_s(m,0)$ and $b_h(m,0)$ respectively.

Based on (14), the following estimate $\tilde{h}(n)$ of the TAR (h(n)) is obtained through inverse complex operations as defined by:

$$\tilde{h}(n) = F^{-1}\{e^{F\{\hat{h}(m)\}}\}, \quad (22)$$

where F and $F^{-1}$ respectively denote the Fourier transform and its inverse, and, $$\hat{h}(m) = \begin{cases} b_h(m, 0) & m > 0 \\ 0 & m = 0 \\ b_h(-m, 0) & m < 0. \end{cases} \quad (23)$$

APPENDIX B

The third order cumulants [14] $c_h(\tau, \rho)$ of the TAR (h(n)) is defined as:

$$c_h(\tau, \rho) = E\{h(n)h(n+\tau)h(n+\rho)\}, \quad (24)$$

where $E\{.\}$ denotes the expectation operator.

The bispectrum $C_h(f_1, f_2)$ [15] of h(n) is defined to be the Fourier transform of the third order cumulant $C_h(\tau, \rho)$. Converting (17) to the bispectrum domain results in:

$$C_h(f_1, f_2) = H(f_1)H(f_2)H^*(f_1+f_2), \quad (25)$$

H(f) is the spectrum of h(n), "•" denotes conjugate.

REFERENCES

The references made to the following articles are not to be taken as any suggestion or admission that the articles form part of the common general knowledge. The content of each article is incorporated herein in its entirety by reference for all purposes.

[1] T. Young, M. Palta, J. Dempsey, J. Skatrud, S. Weber, S. Badr. (1993, April) "The Occurrence of Sleep-Disordered Breathing among middle aged adults". *New England Journal Med* 328(17): 1230-1235.

[2] Proposal for a National Sleep Health Agenda—June 2003 THE BOSTON CONSULTING GROUP

[3] W. W. Flemons, J. A. Rowley, W. M. Anderson, R. D. McEvoy. (2003) "Home Diagnosis of Sleep Apnea: A Systematic Review Co-sponsored by the American Academy of Sleep medicine, The American College of Chest Physicians and the American Thoracic Society", Chest, vol. 124(4), pp. 1543-1579.

[4] The National Sleep Disorders Research Plan, National Institute of Health, USA, 2003.

[5] F. G. Issa, D. Morrison, E. Hadjuk, A. Iyer, T. Feroah, J. E. Remmers "Digital Monitoring of Obstructive Sleep-Apnea Using Snoring Sound and Arterial Oxygen-Saturation" Sleep, vol. 16(8), pp. S132-S132, 1993.

[6] D. L. Van Brunt, K. L. Lichstein, S. L. Noe, R. N. Aguillard and K. W. Lester, (1997) "Intensity Pattern of Sleep Sounds as a Predictor for Obstructive Sleep Apnea", *Sleep*, vol. 20(12), pp. 1151-1156.

[7] T. H. Lee and U. R. Abeyratne, "Analysis of Snoring Sounds for the Detection of Obstructive Sleep Apnea" Med. & Biol. Eng. Comput., Vol. 37, suppl. 2, pp. 538-539, November 1999.

[8] J. Sola-Soler, R. Jané, J. A. Fiz, J. Morera. "Variability of snore parameters in time frequency domains in snoring subjects with and without Obstructive Sleep Apnea" Proceedings of the $27^{th}$ Ann. Intl. Conf. of the IEEE EMBS 2005, pp. 2583-2586.

[9] U. R Abeyratne, A. S Wakwella and C. Hukins, "Pitch jump probability measure for the analysis of snoring sound in apnea", Physiol. Meas., Vol. 26 (5), pp. 779-798, 2005.

[10] J. Sola-Soler, R. Jane, J. A. Fiz, J. Morera. "Automatic classification of subjects with and without Sleep Apnea through snoring analysis" Proceedings of the $29^{th}$ Ann. Intl. Conf. of the IEEE EMBS 2007, pp. 6093-6096.

[11] U. R. Abeyratne, A. S. Karunajeewa and C. Hukins, "Mixed-phase modeling in snore sound analysis", Med. Biol. Eng. Comput. Vol. 45 (8), pp. 791-806, 2007.

[12] A. S. Karunajeewa, U. R. Abeyratne and C. Hukins, "Silence Breathing Snore classification from Snore Related Sounds" Physiol. Meas., Vol. 29 (2), pp. 227-243, 2008.

[13] E., Skoog L, Isberg P, De Smet F, De Moor B, Olofsson P, Gudmundsson S, Valentin L. An algorithm including results of gray scale and power Doppler ultrasound examination to predict endometrial malignancy in women with postmenopausal bleeding. *Ultrasound Obstet Gynecol* 2002; 20: 370-376.

[14] Freedland S J, Isaacs W B, Mangold L A, Yiu, S K, Grubb K A, Partin A W, Epstein J I, Walsh P C, Platz E A. Stronger association between obesity and biochemical progression after radical prostatectomy among men treated in the last 10 years. *Clin Cancer Res* 2005; 11: 2883-2888.

[15] Timmerman D, Testa A C, Bourne T, Ferrazzi E, Ameye L, Konstantinovic M L, Van Calster B, Collins W P, Vergote I, Van Huffel S, Valentin L. Logistic regression model to distinguish between the benign and malignant adnexal mass before surgery: a multicenter study by the International Ovarian Tumor Analysis Group. *J Clin Oncol* 2005; 23: 8794-8801.

[16] C. L. Nikias and A. P. Petropulu, Higher-order spectra analysis: A nonlinear signal processing framework, Englewood Cliff, N.J.: Prentice Hall, 1993.

[17] U. R. Abeyratne, "Blind Reconstruction of non-Minimum Phase Systems from 1-D Oblique Slices of the Bispectrum", IEE Proceedings in Vision, Image and Signal Processing, vol. 146(5), pp. 253-26, October 1999.

[18] T. H. Lee, U. R. Abeyratne, K. Puvanendran and K. L. Goh, "Formant-Structure and Phase-coupling analysis of Human Snoring Sounds for the Detection of Obstructive Sleep Apnea" Computer Methods in Biomechanics and Biomedical Engineering-3, J. Middletion, M. L. Jones and G. N. Pande (eds.), Gordon & Breach Science Publishers, Amsterdam, Netherland, 2000.

[19] J. Duran, S. Esnaola, R. Rubio, A. Iztueta, "Obstructive Sleep Apneahypopnea and related clinical features in a population-based sample of subjects aged 30 to 70 yr," *Am J Respir Crit Care Med*, vol. 63, pp. 685-689, 2001.

[20] K. Banno, M. H. Kryger, "Sleep Apnea: Clinical investigations in humans," *Sleep. Med*, vol. 8, pp. 400-426, 2007.

[21] American Academy of Sleep Medicine Task Force, "Sleep related breathing disorder in adults: Recommendations for syndrome definition and measurement techniques in clinical research", *Sleep* 1999; 22: 667-689.

[22] H. Nakano, M. Hayashi, E. Ohshima, N. Nishikata, T. Shinohara, "Validation of a new system of tracheal sound analysis for the diagnosis of sleep apnea-hypopnea syndrome,", *Sleep*, vol. 27, pp. 951-957, 2004.

[23] C. Guilleminault, R. Stoohs, T. Shiomi, C. Kushida, I. Schnittger, "Upper airway resistance syndrome, nocturnal blood pressure monitoring, and borderline hypertension," *Chest*, vol. 109, pp. 901-908, 1996.

[24] R. D. Chervin, "Sleepiness, fatigue, tired, and lack of energy in obstructive sleep apnea," Chest, vol. 118, pp. 372-379, 2000.

[25] M. Cavusoglu, M. Kamasak, O. Erogul, T. Ciloglu, Y. Serinagaoglu, T. Akcam, "An efficient method for snore/non-snore classification of sleep sounds," *Physiological Measurement*, vol. 28, pp. 841-853, 2007.

[26] Duckitt W D, Tuomi S K and Niesler T R 2006 Automatic detection, segmentation and assessment of snoring from ambient acoustic data *Physiol. Meas.* 27 1047-56.

[27] J. Sola-Soler, R. Jane, J. Morera, "Spectral envelope analysis in snoring signals from simple snorers and patients with obstructive sleep apnea," in *Proc. IEEE 25th Annu. Intl. Conf. Eng. Med. Bio. Soc.*, vol. 3, pp. 2527-2530, 2003.

[28] Schwab R J, Gupta K B, Gefter W B, Metzger L J, Hoffman E A, Pack A I. Upper airway and soft tissue anatomy in normal subjects and patients with sleep-disordered breathing. Significance of the lateral pharyngeal walls. Am J Respir Crit Care Med. 1995; 152:1673-89.

[29] Abeyratne U R, Patabandi C K K and Puvanendran K 2001 Pitch-jitter analysis snoring signals in the diagnosis of obstructive sleep apnea presented at the 23*rd Ann. Int. Conf. IEEE Engineering in Medicine and Biology Soc.* (*IEEE EMBC*2001) (Istanbul, Turkey)

[30] Agrawal, S., P. Stone, K. McGuinness, J. Morris, and A. E. Camilleri. Sound frequency analysis and the site of snoring in natural and induced sleep. Clin. Otolaryngol. Allied Sci. 27(3):162-166, 2002.

[31] Elsayed, M. A. K. Use of wavelet bicoherence in analyzing nonlinear wind-wave interaction during wave growth. J. Coast. Res. 23(6):1593-1601, 2007.

[32] A K Ng, T S Koh, E Baey, T H Lee, U. R. Abeyratne, K Puvanendran, "Could formant frequencies of snore signals be an alternative means for the diagnosis of obstructive sleep apnea?", Sleep Medicine, Elsevier Publishers, in press (Accepted on Jul. 18, 2007, doi:10.1016/j.Sleep.2007.07.010)

[33] U. R. Abeyratne, "A Framework for Information Processing in the Diagnosis of Sleep Apnea", in Encyclopedia of Healthcare Information Systems (ISBN: 978-1-59904-889-5), 2007.

[34] Benesty, J., M. M. Sondhi, and Y. Huang. Springer Handbook of Speech Processing. Springer, 2008.

[35] Huang, Y., A. Malhotra, and D. P. White. Computational simulation of human upper airway collapse using a pressure-/state-dependent model of genioglossal muscle contraction under laminar flow conditions. J. Appl. Physiol. 99(3):1138-1148, 2005.

[36] Shama, K., A. Krishna, and N. U. Cholayya. Study of harmonics-to-noise ratio and critical-band energy spectrum of speech as acoustic indicators of laryngeal and voice pathology. Eurasip J. Adv. Sig. Process., 2007. doi: 10.1155/2007/85286.

[37] Teager, H. M. and S. Teager. Evidence for nonlinear sound production mechanisms in the vocal tract. In: Speech Production and Speech Modeling, edited by W. J. Hardcastle and A. Marchal. London: Kluwer Academic, 1990, pp. 241-262.

[38] Larsen, Y., and A. Hanssen. Wavelet-polyspectra: analysis of non-stationary and non-Gaussian/non-linear signals. In: Proc. IEEE Workshop Stat. Sig. Array Process., 2000, pp. 539-543.

In the present specification and claims, the word "comprising" and its related and derivative terms, including "comprises" and "comprise", are to be interpreted in an inclusive sense as including each of the stated integers but without excluding the inclusion of one or more further integers.

In compliance with the statute, the invention has been described in language more or less specific to structural or methodical features. It is to be understood that the invention is not limited to specific features shown or described since the means herein described comprises preferred forms of putting the invention into effect. The invention is, therefore, claimed in any of its forms or modifications within the proper scope of the appended claims appropriately interpreted by those skilled in the art.

The invention claimed is:

1. A method for diagnosing a sleeping disorder in a subject including:
   processing a digitized audio signal from the subject with at least one electronic processor, said processing including:
   estimating values for parameters of said audio signal;
   applying the values to a predetermined diagnostic model; and
   indicating the presence of a sleeping disorder based on the output of said model;
   wherein the parameters include two pitch parameters, two bispectral parameters, four mel-frequency cepstral coefficients, and three diagonal slice parameters.

2. A method according to claim 1, wherein the parameters further include a Gaussianity distribution parameter that comprises a non-Gaussianity index.

3. A method according to claim 1, wherein the predetermined diagnostic model comprises a logistic regression model.

4. A method according to claim 1, wherein the step of processing the digitized audio signal from the subject includes dividing the digitized signal into a plurality of segments.

5. A method according to claim 4, including identifying said segments indicating voiced snoring prior to the step of estimating values for the plurality of parameters.

6. A method according to claim 1, wherein the presence of the sleeping disorder is indicated on an electronic display coupled to a computer incorporating the at least one electronic processor.

7. A method according to claim 1, wherein the parameters further include a Gaussianity distribution parameter and wherein the method includes: dividing the digitized audio signal into a number of segments; calculating indices indicating a degree of Gaussianity corresponding to each of the segments; and computing a parameter indicating overall Gaussianity of the said signal based on the indices.

8. A method according to claim 7, wherein the step of calculating indices indicating a degree of Gaussianity includes calculating a normal probability of each said segment of the digitized audio signal.

9. A method according to claim 7, including a step of pre-emphasis filtering of the digitized audio signal to relatively boost energy of portions of the digitized audio signal corresponding to snoring episodes of the subject.

10. A method according to claim 9, wherein the step of pre-emphasis filtering of the digitized audio signal includes applying a digital high pass filter to said signal.

11. A method according to claim 7, including a step of comparing the indices indicating a degree of Gaussianity to a predetermined threshold value.

12. A method according to claim 11, including processing a user input to select the predetermined threshold value from a range of predetermined threshold values calculated to optimize for desired negative predictive values and positive predictive values.

13. A method according to claim 7, including a step of discarding first and last portions of the digitized audio signal contaminated with non-sleep related noise.

14. An apparatus for diagnosing a sleeping disorder in a subject including:
- at least one digital signal input point for receiving a digitized audio signal of the subject;
- at least one electronic processor in communication with the digital signal input point;
- a user display viewable by an operator of the apparatus; and
- at least one electronic memory in communication with the electronic processor, said electronic memory containing tangible instructions executable by the said electronic processor, said instructions being;
- to detect snore segments of the digitized audio signal;
- to estimate values for a plurality of parameters of the snore segments, said parameters including two pitch parameters, two bispectral parameters, four mel-frequency cepstral coefficients, and three diagonal slice parameters;
- to apply the values to a predetermined diagnostic model; and
- to indicate the presence of a sleeping disorder based on the model upon the user display.

15. An apparatus for diagnosing a sleeping disorder in a subject including:
- at least one audio signal input point for receiving an audio signal of a sleeping subject;
- an analog to digital converter coupled to the audio signal input point to create a digitized audio signal;
- a plurality of sleep-related parameter calculation modules responsive to the digitized audio signal and arranged to produce signals indicating values for sleep-related parameters including two pitch parameters, two bispectral parameters, four mel-frequency cepstral coefficients, and three diagonal slice parameters;
- a classification module responsive to the signals indicating values for said sleep-related parameters and arranged to classify the audio signal as either sleep dysfunctional or non-sleep dysfunctional;
- a display assembly responsive to the classification module and arranged to display said classification.

16. An apparatus according to claim 15, wherein the assembly includes a data logger to record the digitized audio signal and to record the signals indicating values for said sleep-related parameters.

17. An apparatus according to claim 15, wherein the assembly includes a segmentation module arranged to segment the digitized audio signal, said segmentation module being disposed in a signal path between the analog to digital converter and the plurality of sleep-related parameter calculation modules.

18. An apparatus according to claim 15, wherein the sleep-related parameter calculation modules include one or more of: a total airways response calculator; a pitch calculator; a cepstral coefficient calculator; non-Gaussianity Index calculator.

19. An apparatus according to claim 15, wherein the sleep related parameter calculation modules include the non-Gaussianity Index (NGI) calculator and further including a pre-emphasis module coupled to an input side of the NGI calculator for filtering the digitized audio signal prior to processing by the NGI calculator.

20. An apparatus according to claim 15 including a user control interface coupled to modules of the apparatus to facilitate operator adjustment of said modules.

21. A computer software product comprising a program storage device, readable by machine, tangibly embodying a program of non-transitory instructions executable by the machine to cause the machine to perform a method according to claim 1.

22. A method for producing a diagnostic model to identify a sleep disorder including:
- compiling data from a training set of subjects including subjects known to suffer from the sleep disorder and subjects known to not suffer from the disorder;
- processing the data with an electronic processor to generate values for a plurality of parameters corresponding to the data and characterising the Pitch and Total Airways Response of the subjects, said plurality of parameters including two pitch parameters, two bispectral parameters, four mel-frequency cepstral coefficients, and three diagonal slice parameters;
- calculating classification model parameters from said values;
- displaying the classification model parameters for use by a human operator.

23. A method according to claim 22, wherein the diagnostic model is a logistic regression model and where the step of calculating classification model parameters from said values includes applying logistic regression analysis to the values.

* * * * *